(12) United States Patent
Plebanski

(10) Patent No.: US 8,846,026 B2
(45) Date of Patent: Sep. 30, 2014

(54) COMPOSITION COMPRISING IMMUNOGENIC MICROPARTICLES

(75) Inventor: Magdalena Plebanski, Clifton Hill (AU)

(73) Assignee: PX Biosolutions Pty Ltd, Clifton Hill, Victoria (AU)

( * ) Notice: Subject to any disclaimer, the term of this patent is extended or adjusted under 35 U.S.C. 154(b) by 201 days.

(21) Appl. No.: 13/283,294

(22) Filed: Oct. 27, 2011

(65) Prior Publication Data

US 2012/0082725 A1 Apr. 5, 2012

Related U.S. Application Data

(60) Division of application No. 12/603,439, filed on Oct. 21, 2009, now Pat. No. 8,287,877, which is a continuation of application No. 10/380,588, filed as application No. PCT/AU01/01160 on Sep. 14, 2001, now abandoned.

(30) Foreign Application Priority Data

| Sep. 14, 2000 | (AU) | PR0117 |
|---|---|---|
| May 10, 2001 | (AU) | PR4888 |
| May 14, 2001 | (AU) | PR4962 |

(51) Int. Cl.
  *A61K 39/00* (2006.01)
  *A61K 38/00* (2006.01)
  *G01N 33/543* (2006.01)

(52) U.S. Cl.
  CPC .............. *A61K 39/00* (2013.01); *A61K 2039/60* (2013.01)
  USPC ...................... 424/93.1; 424/179.1

(58) Field of Classification Search
  CPC .................. A61K 9/1647; A61K 2039/55555; A61K 39/0011; A61K 39/39; A61K 47/48915; A61K 9/5153; A61K 2039/6087; A61K 9/0019; A61K 9/167; A61K 39/00; A61K 2039/5156; A61K 47/48869; A61K 2039/5158; A61K 2039/55516; C12N 11/00
  See application file for complete search history.

(56) References Cited

U.S. PATENT DOCUMENTS

| 4,035,316 A | 7/1977 | Yen et al. |
|---|---|---|
| 4,157,323 A | 6/1979 | Yen et al. |
| 4,170,685 A | 10/1979 | Rembaum et al. |
| 4,225,581 A | 9/1980 | Kreuter et al. |
| 4,247,434 A | 1/1981 | Vanderhoff et al. |
| 4,269,821 A | 5/1981 | Kreuter et al. |
| 4,438,239 A | 3/1984 | Rembaum et al. |
| 4,828,984 A | 5/1989 | Schwartz |
| 5,002,883 A | 3/1991 | Bieniarz et al. |
| 5,178,882 A | 1/1993 | Kossovsky et al. |
| 5,219,577 A | 6/1993 | Kossovsky et al. |
| 5,334,394 A | 8/1994 | Kossovsky et al. |
| 5,443,832 A | 8/1995 | Amerongen et al. |
| 5,665,582 A | 9/1997 | Kausch et al. |
| 5,688,761 A | 11/1997 | Owen et al. |
| 5,789,261 A | 8/1998 | Schwartz |
| 5,871,747 A | 2/1999 | Gengoux-Sedlik et al. |
| 5,928,647 A | 7/1999 | Rock |
| 5,961,970 A | 10/1999 | Lowell et al. |
| 5,985,284 A | 11/1999 | Lowell |
| 6,129,916 A | 10/2000 | Chang |
| 6,149,922 A | 11/2000 | Balasubramanian et al. |
| 6,153,201 A | 11/2000 | Rose et al. |
| 6,287,588 B1 | 9/2001 | Shih et al. |
| 6,338,853 B1 | 1/2002 | Bystryn |
| 6,352,697 B1 | 3/2002 | Cox et al. |
| 6,506,386 B1 | 1/2003 | Friede et al. |
| 6,551,597 B1 | 4/2003 | Harrison et al. |
| 7,247,310 B1 | 7/2007 | Ohno et al. |
| 8,287,877 B2 | 10/2012 | Plebanski |
| 2007/0059681 A1 | 3/2007 | Ataman-Onal et al. |
| 2007/0275007 A1 | 11/2007 | Barchi et al. |
| 2008/0031899 A1 | 2/2008 | Reddy et al. |
| 2008/0241259 A1 | 10/2008 | Ataman-Onal et al. |
| 2009/0169636 A1 | 7/2009 | O'Hagan et al. |
| 2009/0202651 A1 | 8/2009 | Moody et al. |
| 2009/0209905 A1 | 8/2009 | Strong |
| 2010/0021548 A1 | 1/2010 | O'Hagan et al. |
| 2010/0136036 A1 | 6/2010 | Yang |
| 2010/0151031 A1 | 6/2010 | DeSimone et al. |
| 2010/0233251 A1 | 9/2010 | Von Andrian et al. |
| 2010/0278919 A1 | 11/2010 | Denes et al. |
| 2010/0285132 A1 | 11/2010 | Higbee et al. |
| 2010/0285135 A1 | 11/2010 | Wendorf et al. |

FOREIGN PATENT DOCUMENTS

| EP | 180564 | 7/1991 |
|---|---|---|
| EP | 1 326 633 B1 | 3/2011 |
| GB | 1544107 | 4/1979 |
| WO | WO 91/06282 | 5/1991 |

(Continued)

OTHER PUBLICATIONS

Sweiggard et al. Cellular immunology, 1995, vol. 165, pp. 302-311.*
Garnier et al. Journal of Immunology, 2005, vol. 175, No. 3, pp. 1609-1618.*
McCully et al. Peritoneal Dialysis International, 2006, vol. 26, pp. 8-25.*
"Virus (biology)" Encyclopedia Britannica. On line, Encyclopadia Britanica Inc. 2014. pp. 1-19.*
AbD serotec by ab-direct.com, searched by 2007.
Adler, et al., "Immunity and Vaccine Development in Pasteurella Multocida Infections," *J. Biotechnol*, 44(1-3):139-44 (1996).
Benns, et al., "Tailoring New Gene Delivery Designs for Specific Targets," *Journal of Drug Targeting*, 8(1):1-12 (2000).

(Continued)

*Primary Examiner* — Bao Li
(74) *Attorney, Agent, or Firm* — Hamilton, Brook, Smith & Reynolds, PC

(57) ABSTRACT

The invention provides an immunogenic composition comprising at least one antigen in association with microparticles, wherein the microparticles are in the same size range as viruses. In addition the invention also provides vaccine compositions and methods of eliciting immune responses in a subject.

24 Claims, 24 Drawing Sheets

(56) References Cited

FOREIGN PATENT DOCUMENTS

| | | |
|---|---|---|
| WO | WO 91/16072 | 10/1991 |
| WO | WO 96/14855 | 5/1996 |
| WO | WO 96/20698 | 7/1996 |
| WO | WO 97/03702 | 2/1997 |
| WO | WO 98/01161 | 1/1998 |
| WO | WO 99/09956 | 3/1999 |
| WO | WO 99/36090 | 7/1999 |
| WO | WO 99/43349 | 9/1999 |
| WO | WO 00/12124 | 3/2000 |
| WO | WO 00/46147 | 8/2000 |
| WO | WO 00/74658 | 12/2000 |
| WO | WO 01/24834 | 4/2001 |
| WO | WO 01/52884 | 7/2001 |
| WO | WO 01 52884 A1 | 7/2001 |
| WO | WO 01/70200 | 9/2001 |
| WO | WO 02/22164 A1 | 3/2002 |
| WO | WO 2008/031126 A1 | 3/2008 |
| WO | WO 2009/108807 A1 | 9/2009 |
| WO | WO 2010 085509 A1 | 7/2010 |

OTHER PUBLICATIONS

Blake, et al., "The Importance of Exogenous Antigen in Priming the Human CD8+ T Cell Response: Lessons From the EBV Nuclear Antigen EBNA1," *J. Immunol.*, 165:7078-7087 (2000).

Coombes, et al., "Resorbable Lamellar Particles of Polylactide as Adjuvants for Influenza Virus Vaccines," *Biomaterials*, 19(11-12):1073-81 (1998).

Dendritic Cell by free encyclopedia by Answer.com, 1-5 (2007).

Desai, et al., "Immune Response With Biodegradable Nanosperes and Alum: Studies in Rabbits Using Staphylococcal Enterotoxin B-Toxoid," *Journal of Microencasulation*, 17(12): 215-225 (Mar.-Apr. 2000).

Frey, et al., "Immunization of Mice With Peptomers Covalently Coupled to Aluminum Oxide Nanoparticles," *Vaccine*, 17:3007-3019 (1999).

Hiltbold, et al., "Presentation of MUC1 Tumor Antigen by Class I MHC and CTL Function Correlate With the Glycosylation State of the Protein Taken Up by Dendritic Cells," *Cellular Immunol*, 194:143-149 (1999).

Hussain, et al., "Enhanced Oral Uptake of Tomato Lectin-Conjugated Nanoparticles in the Rat," *Pharmaceutical Research*, 14(5):613-618 (1997).

Jarrett, et al., "Size-Controlled Synthesis of Dextran Sulfate Coated Iron Oxide Nanoparticles for Magnetic Resonance Imaging," *Nanotechnology*, 18:35603 (2007).

Kersten, et al., "Liposomes and ISCOMS as Vaccine Formulations," *Biochim. Biophys. Acta*, 1241:117-138 (1995).

Konno, et al., "Enzymatic Activation of Oleuropein: A Protein Crosslinker Used as a Chemical Defense in the Privet Tree," *Proc. Natl. Acad. Sci.*, 96:9159-9164 (1999).

Kupfer Cells by free encyclopedia by Answer.com, 1-2 (2007).

Lehmann, et al., "Functional Assays for Evaluation of Serogroup B Meningococcal Structures as Mediators of Human Opsonophagocytosis," *J. Immunol Methods*, 200(1-2):55-68 (1997).

McCluskey, et al., "T Cell Activation by Purified, Soluble, Class I MHC Molecules. Requirement for Polyvalency," *J. Immunol*, 141(5):1451-1455 (1988).

Reddish, et al. "Anti-Muc1 Class I Restricted Ctls in Metastatic Breast Cancer Patients Immunized With a Synthetic Muc1 Peptide," *Int. J. Cancer*, 76:817-823 (1998).

Sharp, et al., "Uptake of Particulate Vaccine Adjuvants by Dendritic Cells Activates the NALP3 Inflammasome," *PNAS*, 106(3):870-875 (2009).

Shek, et al., "Immune Response Mediated by Liposome-Associated Protein Antigens," *Immunology*, 50:101-106 (1983).

Tabata, et al.,"Size Effect on Systemic and Mucosal Immune Responses Induced by Oral Administration of Biodegradable Microspheres," *Vaccine*, 14(17-18):1677-1685 (1996).

Thiele, et al., "Evaluation of Particle Updatke in Human Blood Monocyte-Derived Cells in Vitro. Does Phagocytosis Activity of Dendritic Cells Measure up with Macrophages?" *Journal of Controlled Release*, 76:59-71 (2001).

Tobio, et al., "Stealth PLC-PEG Nanoparticles as Protein Carrieres for Nasal Administration," *Pharmaceutical Research*, 15(2):270-275 (1998).

Trubetskoy, et al., "Self-Assembly of DNA-Polymer Complexes Using Template Polymerization," *Nucleic Acids Res.*, 26(18):4178-85 (Sep. 15, 1998).

Verrecchia, et al., "Non-Stealth (Poly(Lactic Acid/Albumin)) and Stealth (Poly(Lactic Acidpolycthylcnc Glycol)) Nanoparticles as Injectable Drug Carriers," *Journal of Controlled Release*, 36(1-2):49-61 (1995).

Villacres-Eriksson, et al., "Antigen Presentation by Naïve Macrophages, Dendritic Cells and B Cells to Primed T Lymphocytes and Their Cytokine Production Following Exposure to Immunostimulating Complexes," *Clin. Exp. Immuno.*, 102:46-52 (1995).

"EDAC (carbodiimide) Heterobifunctional cross-linker: Product Description," *Uptima*, 4 pages, date unknown.

Yang, et al., "Application of the ELISPOT Assay to the Characterization of CD8+ Responses to Epstein-Barr Virus Antigens," *Blood*, 95(1):241-248 (1999).

Ozel, et al., "Quaternary Structure of the Immunostimulating Complex (Iscom)," *J. Ultra and Mole. Struc. Res.*, 102(3):240-248 (1989).

Chen, S.C., et al., "Protective Immunity Induced by Oral Immunization With a Rotavirus DNA Vaccine Encapsulated in Microparticles," *J. Virol.* 72(7):5757-5761 (1998).

Harding, C.V. and Song, R., "Phagocytic Processing of Exogenous Particulate Antigens by Macrophages for Presentation by Class I MHC Molecules," *J. Immunol.* 153:4925-4933.

Lo-Man, R., et al., "A Recombinant Virus-Like Particle System Derived From Parvovirus as an Efficient Antigen Carrier to Elicit a Polarized Th1 Immune Response Without Adjuvant," *Eur. J. Immunol.* 28:1401-1407 (1998).

Xiang, S.D., et al., "Promising Particle-Based Vaccines in Cancer Therapy," *Expert Rev. Vaccines* 7(7):1103-1119 (2008).

Supplementary European Search Report, EP 01 96 6829, dated Mar. 31, 2006.

International Search Report, PCT/AU01/01160, mailed Nov. 15, 2001.

International Preliminary Examination Report, PCT/AU01/01160, dated Jan. 7, 2003.

Cochlovius, B., et al., "In Vitro and In Vivo Induction of a Th Cell Response Toward Peptides of the Melanoma-Associated Glycoprotein 100 Protein Selected by the TEPITOPE Program", *J. Immunology*, 165:4731-4741 (2000).

Hussain, N., et al., "Enhanced Oral Uptake of Tomato Lectin-Conjugated Nanoparticles in the Rat," *Pharmaceutical Research*, 14(5):613-618 (1997).

Frey, A., et al., "Immunization of Mice With Peptomers Covalently Coupled to Aluminum Oxide Nanoparticles," *Vaccine*, 17:3007-3019 (1999).

McCluskey, J., et al., et al., "T Cell Activation by Purified, Soluble, Class 1 MHC Molecules," J. Immunol, 141(5):141-145 (1988).

Office Action From U.S. Appl. No. 12/603,439, Dated May 12, 2011.

Sjölander, S. et al., "Induction of homologous virus neutralizing antibodies in guinea-pigs immunized with two human immunodeficiency virus type 1 glycoprotein gp120-iscom preparations. A comparison with other adjuvant systems," *Vaccine*, 14(4): 344-352 (1996).

Sjölander, S. et al.,"ISCOMs: an adjuvant with multiple functions," *J. Leuko. Biol.*, 64: 713-723 (Dec. 1998).

The Free Dictionary by Farlex, pp. 1-4, Retrieved from the internet on Nov. 3, 2011 from: http://www.thefreedictionary.com/about/.

Office Action U.S. Appl. No. 12/603,439 dated Nov. 8, 2011.

Notice of Allowance, U.S. Appl. No. 12/306,439 dated Jun. 27, 2012.

\* cited by examiner

C

D

A

B

A

B

A

COMPOSITION COMPRISING IMMUNOGENIC MICROPARTICLES

RELATED APPLICATION(S)

This application is a divisional of U.S. application Ser. No. 12/603,439, filed Oct. 21, 2009, now U.S. Pat. No. 8,287,877 which is a continuation of U.S. application Ser. No. 10/380,588, filed Jun. 30, 2003, now abandoned which is the U.S. National Stage of International Application No. PCT/AU01/01160, filed on Sep. 14, 2001, published in English. The entire teachings of the above applications are incorporated herein by reference. PCT/AU01/01160 claims the benefit of AU PR 0117, filed Sep. 14, 2000, AU PR 4888, filed May 10, 2001 and AU PR 4962, filed May 14, 2001.

FIELD OF INVENTION

The present invention relates to immunogenic compositions, vaccine compositions, methods of eliciting immune responses in a subject and methods of producing the compositions.

BACKGROUND OF THE INVENTION

Manipulation of the immune systems of humans and animals is a recognised manner of avoiding or treating certain diseases or conditions.

The mechanisms by which the immune system controls disease include the induction of neutralising antibodies (a humoral immune response), and the generation of cellular or T-cell responses. The latter include T-helper cells ($T_H$) and cytotoxic T-lymphocytes (CTL). In instances of viral infection e.g. polio or hepatitis, antibodies provide protection by preventing the virus from infecting cells. Antibodies can also protect against bacteria e.g. pneumococci and staphylococci, by use of bactericidal mechanisms and by neutralising bacterial toxins.

T-cells can be stimulated when peptide fragments from an antigen are bound to molecules known as MHC I or MHC II (major histocompatability complex, class I or class II) and are displayed on the surface of professional APCs (antigen presenting cells) such as DCs (dendritic cells) or macrophages. The T-cells contain antigen receptors which they employ to monitor the surface of cells for the presence of the peptide fragments from the antigen. The antigen receptors on $T_H$ cells recognise antigenic peptides bound to MHC II molecules. By contrast, the receptors on CTLs react with antigens displayed on class I molecules.

The stimulated T-cells amplify the immune response in that when a T-cell recognises a target cell which is infected with the pathogen, or that contain an epitope which it recognises, a chain of events is triggered and these eventually result in death of the infected cells. In addition, some T-cells can stimulate secretion of cytokines or lymphokines, which in turn can exert effects that ultimately lead to inactivation or eradication of pathogens.

Although there are many vaccines on the market there is a need to produce more effective and broad ranging vaccines for a number of diseases or conditions. There also remains a need for protection against infective agents or pathogens against which vaccines are currently unavailable or ineffective. In addition, there is a need for effective, single-dose vaccines, which are particularly desirable for economic reasons, for ease of delivery, and for patient or subject compliance.

Most vaccines suffer from the disadvantage that they are not able to induce an optimal combination of the various types of humoral and cellular responses so as to be immunologically effective. For instance, some vaccines only stimulate antibody responses when both antibody and cellular responses would be more efficacious. In other instances, multiple doses of the vaccines eg booster shots are required in order to attain protection against the relevant infective agent.

In some other instances, IgE production is induced along with other desired immunoglobulins such as IgA, IgG and IgM. Vaccines that induce IgE are not desirable, as the immunoglobulin is involved in allergic responses.

Stimulation of IgA production is a "first line" defense for pathogens that infect via entry through a mucosal site or surface. Thus, vaccines that can generate a high IgA secretory immune response without enhancing IgE production would also be valuable.

In yet other instances, although a vaccine results in stimulation of APCs, the degree of immune stimulation is suboptimal. For example, dendritic cells or DCs are characterised by a series of subset of cells that can be distinguished from each other by surface molecules some of which are specific ligands that bind receptors on T cells. Accordingly, it would be desirable to produce a vaccine which would selectively target a subset of DCs, eg a subset capable of efficient CD8 T-cell priming since these T-cells play a vital role in protective immunity against many intracellular pathogens and cancer, but are notoriously difficult to induce.

Further, with regard to vaccines extracellular antigens traditionally do not enter the MHC-I processing pathway in most cells. In general, the production of CTL immunity using nonliving vaccines is unlikely although alternative routes of processing and presentation for class 1 have been proposed in APC through the uptake of apoptotic cells, immune complexes and particles [1]. Non-infective viral like particles (VLP) composed of the surface Hepatitis B protein or yeast retro-transposon protein particles have been shown to be efficiently processed for MHC I presentation by macrophages to induce CD8 CTL responses in vitro and in vivo [2, 3]. VLPs are multimeric, lipid-containing protein particles the lipid content of which comprises more than 50% of the dry weight.

However, since Hepatitis B core protein particles fail to be immunogenic, and have a lower lipid content, it has been proposed that VLP are immunogenic not by virtue of size, but by biochemical composition. This would be consistent with the proposal that when antigen is presented in formulations containing lipid or detergent, they are able to fuse with the APC, possibly by damaging the cell membrane, and thus gain entry into the cytoplasm.

The use of microspheres within which are entrapped antigens have been explored as a possible vaccine composition. The microspheres are made from biodegradable polyesters of lactic and glycolic acids (PLA and PLGA). The microspheres are constructed such that their size and polymer composition control the rate at which they degrade. As the microspheres degrade, the entrapped antigen is released therefrom, and provides for a controlled release of antigen for stimulating the immune response. It is unlikely that these molecules would interface and react with immune cells in the same way as protein particles the make-up of which are biologically compatible with cellular membranes.

However, the difficulties with this form of vaccine composition include antigen stability, the size of the spheres and the antigen-release kinetics, all of which still need to be resolved so as to produce a vaccine with good antigenicity and lasting immunogenicity, and to produce a vaccine that can be manufactured and administered economically [4].

In U.S. Pat. No. 4,225,581, a composition comprising a mixture of heterogenous particles ranging in size is described as being useful for delivering antigens that are adsorbed onto the surface of the polymeric particles to the body. However, the successful delivery, antigenicity and immunogenicity of such a vaccine was not illustrated or shown. Specifically, there was no reference to the induction of CD8 T cell responses, or even processing into the MHC class I presentation pathway. The polymeric material of the particles would be expected to have similar characteristics as PLA or PLGA microparticles discussed above.

Thus, it was not known prior to the present invention if the size per se of particles administered as part of vaccines could induce immunogenic responses.

In work leading up to the present invention, the inventor has surprisingly found that microparticles about the same size as viruses associated with an antigen provide strong cellular and humoral antibody responses in subjects.

SUMMARY OF THE INVENTION

In a first embodiment the invention provides an immunogenic composition comprising at least one antigen in association with microparticles wherein the microparticles are in the same size range as viruses.

The term "comprising" used in relation to the immunogenic composition means that the composition includes the antigen and microparticles. It may also include other components.

The term "antigen" refers to any molecule, moiety or entity capable of eliciting an immune response. This includes cellular and/or humoral immune responses. Depending on the intended function of the composition one or more antigens may be included.

The antigen may be a peptide, protein, lipid, carbohydrate, nucleic acid or other type of molecule or a combination of any of these.

The antigen may be derived from a pathogen, tissue, cell, organ or molecule depending on the intended purpose of the composition, and may be a purified antigen, or be of recombinant origin produced in suitable vectors such as bacteria, yeast or cell cultures. The pathogen for example may be any pathogen, intra or extracellular, antigenic portions or parts thereof, viral, bacterial or protozoal in origin such as HIV, influenza viruses, hepatitis viruses, malaria. Specifically, examples of the antigens envisaged by the present invention are as follows: pollens, hepatitis C virus, (HIV) core, E1, E2 and NS2 proteins, antigens from *Plasmodium* species such as *P. vivax* and other *Plasmodium* species including *P. falciparum* circumsporozoite protein (CS) and human *Plasmodium*-falciparum, -vivax, -ovalae and malariae, TRAP, MSP-1, MSP-2, MSP-3, MSP-4, MSP-5, AMA-1, RESA, SALSA, STARP, LSA1 and LSA3, HIV-gp120/160 envelope glycoprotein, *streptococcus* surface protein Ag, influenza nucleoprotein, haemagglutinin-neuraminidase surface infection, TcpA pilin subunit, VP1 protein. LMCV nucleoprotein, *Leishmania major* surface glycoprotein (gp63), *Bordetella pertussis* surface protein, rabies virus G protein, *Streptococcus* M protein, Staphylococcal proteins or *Helicobacter pylori* proteins, Syncytial virus (RSV) F or G proteins, Epstein Barr virus (EBV) gp340 or nucleoantigen 3A, haemagglutinin, *Borrelia burgdorferi* outer surface protein (Osp)A, *Mycobacterium tuberculosis* 38 kD lipoprotein or 30 kD protein (Ag85), 10 kD or 65 kD proteins, *Neisseria meningitidis* class 1 outer protein, Varicella zoster virus IE62 and gpI, Rubella virus capsid protein, Hepatitis B virus pre 51 ag, Herpes simplex virus type I glycoprotein G or gp D or CP27, Murray valley encephalitis virus E glycoprotein, Hepatitis A virus VP1, polio virus capsid protein VP1, VP2, VP3 and VP6, *chlamydia trachomatis* surface protein, Hepatitis B virus envelope Ag pre S2, Human rhinovirus (HRV) capsid, papillomavirus peptides from oncogene E6 and E7, *Listeria* surface protein, Varicella virus envelope protein, Vaccinia virus envelope protein, *Brucella* surface protein, Rotavirus VP-3, VP-4, VP-5, VP-7 and VP-8, a combination of one or more of said antigens, an amino acid subunit of said antigens comprising five or more amino acids in length or combinations of one or more of said subunits.

Lysates or culture filtrates from the pathogens exemplified above may also be used as the antigen. Such fractions may be in purified, concentrated or diluted form, so long as they provide antigenicity and/or immunogenicity. Thus it makes it possible to "tailor-make" an immunogenic composition for a patient in accordance with the invention by using patient tumor lysates or a specific set of tumor proteins conjugated to the microparticles.

The antigen may also be derived from any tumour type or malignancy. Examples of cancer types from which the antigens may be derived are breast, lung, pancreas and colon cancer and melanoma. Some further examples of specific antigens obtained from tumours are melanoma specific antigen (for example, the MAGE series antigen), carcino embryonic antigen (CEA) from colon, nm23 cancer antigen and other cancer antigens or indeed antigens extracted from any tumour, e.g. mucin such as MUC-1 to MUC-7 antigens. Recombinant peptides or proteins alone or in combination may also be used.

The antigen may also be a synthetic epitope such as a mimic or peptidomimetic based on one or more of the antigens referred to above.

The term "in association with" refers to an association between the microparticle and the antigen. This may be by adsorption or by conjugation or covalent coupling. Preferably the antigen is covalently linked to the microparticle. Even more preferably, the antigen is conjugated to the surface of the microparticle.

The term microparticle refers to a small particle. This may be in the form of a bead or sphere or any other suitable shape.

The term "virus sized particles" (VSP) is used in this document to describe certain embodiments of the immunogenic composition of the invention. It should be understood that the term VSP has only been adopted for convenience and does not limit the invention to the size of known viruses. For Example, particles of the same size as unknown viruses are also contemplated by the invention.

Preferably the microparticle has a solid core providing stability to the conjugated or associated antigens as distinct from the microspheres of the prior art which are hollow or encapsulate molecules. For convenience these are referred to herein as virus sized solid particles (VSSP) where the antigen is present on the outside of the particle. The particles used to make VSSP are available from the manufacturer and are substantially of uniform size (i.e., within ±10% of the stated size).

The term "solid core" means substantially solid (i.e. the particles are not hollow). The microparticle may be composed of any suitable material so long as it does not detract from the function of the immunogenic composition. Thus the microparticles may be made from materials such as latex, ferrous molecules, gold (such as gold nanoparticles), glass, calcium phosphate, polystyrene or biodegradable and biocompatible polymers such as PLG (Polylysine g). Preferably, the microparticles are composed of polystyrene, PLG or gold. Most preferably, the microparticles are made from polystyrene.

The microparticle is in the same size range as known viruses. This means that the microparticle is preferably less than about 0.50 µm. Preferably the microparticle is of such a size that it is adapted to elicit an immune response. In particular it is adapted to be taken up by antigen presenting cells within a human subject or an animal. More preferably the microparticles are between about 0.03 and 0.50 µm, preferably about 0.03 and 0.15 µm, still more preferably between about 0.03 and 0.10 µm. Even more preferably the microparticles are about 0.03 to 0.05 µm, more preferably the microparticles are between about 0.03 µm and 0.049 µm, still more preferably the microparticles are between about 0.03 and about 0.04 µm or about 0.04 and 0.049 µm.

In a preferred embodiment, a population of microparticles to be used in accordance with the invention, eg in one dose of vaccination, is of a uniform size. This means that the majority of the particles in a given population are of the stated size.

Preferably the microparticle/antigen composition is particularly adapted to elicit a cellular and/or humoral immune response. The cellular response is preferably selected from the group consisting of activation, maturation or proliferation of $T_H$ cells, in particular IFN and IL4 producing T cells, CTLs, particularly CD8 CTL and B cells. Preferably the microparticle/antigen composition elicits mechanisms for MHC class I presentation of antigens which are taken up by a hitherto unknown mechanism involving caveole and/or clathrin pits for further processing by Rab 4 independent and TAP dependent processes as explained in Examples 4 and 7 herein. The humoral response is preferably selected from the group consisting of IgA, IgD, IgG, IgM and subclasses thereof.

Cells which assist in mounting or amplifying an immune response may also be stimulated by the composition. These included but are not limited to APCs such as DCs of both myeloid or lymphoid origin, and macrophages. The maturation, activation or proliferation of such cells are contemplated, as are the co-stimulatory ligands or molecules on such cells that interact with T-cells, eg CD 40, CD 80 and CD 86.

The immunogenic composition of the invention may be used in treatment, prophylaxis or prevention of the disease or condition caused by, or associated with contact with the antigen. For example, the composition may be used in the treatment or prophylaxis of certain cancers.

In another embodiment the invention provides a vaccine composition comprising microparticles associated with at least one antigen wherein the microparticles are in the same size range as viruses. The composition of the invention is particularly useful and advantageous as it is an effective single-dose vaccine but may also be used in multiple dose regimes.

Thus, in one embodiment, the invention provides a single-dose vaccine composition comprising microparticles associated with at least one antigen, wherein the microparticles are of the same size range as viruses.

By "single-dose", it is meant that a humoral and/or cellular immune response is stimulated or enhanced to maximal levels ("maximal" means that the levels are not capable of being further increased by repeated vaccination), or affords protection to the recipient of the composition, following one administration of the composition or vaccine. The administration may be by any suitable means eg. by injection i.m., i.p., i.v., orally, by inhalation, or by administration through a mucosal surface or site.

Preferably, the antigen is conjugated to the surface of the microparticles. The size of the microparticles is between about 0.03 and 0.5 µm, preferably about 0.03 to 0.15 µm, more preferably about 0.03 to 0.10 µm even more preferably about 0.03 to 0.05 µm in diameter, even more preferably about 0.03 to 0.049 µm. Still more preferably 0.03 to 0.04 µm or 0.04 to 0.049 µm. The microparticles are most preferably made of polystyrene, PLG, glass, calcium phosphate or gold. In a preferred embodiment, each antigen for use in accordance with the invention is conjugated to microparticles of a uniform size.

In a further embodiment, the invention provides a single-dose vaccine composition that is capable of mounting a humoral and a cellular immune response, the composition comprising microparticles associated with at least one antigen, wherein the microparticles are in the same size range as viruses.

The cellular response is preferably selected from the group consisting of stimulation, maturation or proliferation of $T_H$ cells, CTLs and B cells. The humoral response is preferably selected from the group consisting of IgA, IgG, IgM and subclasses thereof. Preferably, IgG, IgA and/or IgM responses are stimulated.

Cells which assist in mounting or amplifying an immune response may also be stimulated by the composition. These included but are not limited to APCs such as DCs of both myeloid or lymphoid origin, and macrophages. The maturation, activation or proliferation of such cells are contemplated.

The term "comprising" has the same meaning given above.

The term microparticle has the meaning given above. Preferably the microparticle is adapted to be taken up by antigen presenting cells in an animal. Preferably the microparticles are between 0.03 and 0.5 µm, preferably between 0.03 and 0.15 µm. More preferably the microparticles are between about 0.03 and 0.10 µm, more preferably the microparticles are between about 0.03 µm and about 0.05 µm. Still more preferably the microparticles are about 0.03 to 0.049 or 0.04 and 0.049 µm.

The terms "antigen" and "associated with" have the meanings given above. Any suitable antigen may be used depending on which condition/disease it is intended to vaccinate against.

The amount of vaccine composition of the invention delivered to a patient is not critical or limiting. An effective amount of the vaccine composition is that which will stimulate an immune response against the antigen component, preferably after a single dose or administration and desirably, will result in strong cellular and humoral responses. The amount of compositions delivered may vary according to the immune status of the patient (depending on whether the patient is immunosuppressed or immunostimulated), the judgement of attending physician or veterinarian, whether the composition is used as a vaccine to prevent or treat a disease state, or as a vaccine to prevent tumour formation, or whether the vaccine is used in the treatment of an existing tumour. By way of example, patients may receive from 1 µg to 10,000 µg of the composition of the invention, more preferably 50 µg to 5,000 µg, still more preferably 100 µg to 1,000 µg, and even more preferably 100 µg to 500 µg of the composition of the invention. Adjuvants are not generally required. However, adjuvants may be used for immunization. Suitable adjuvants include alum, as well as any other adjuvant or adjuvants well known in the vaccine art for administration to humans.

The vaccine of the invention may be administered by injection, by administration via the oral route, by inhalation or by administration via a mucosal surface or site. In one embodiment, the vaccine is administered by means of a gene gun. Ferrous microparticles and gold microparticles if used in accordance with the invention are especially suitable for administration by gene gun, However, other types of microparticles with antigens may be administered in this manner. For example, antigens derived from malaria libraries, DNA or plasmids have been shown to be effectively administered by gene gun in accordance with the procedure described in Smooker P M et al, "Expression library immunisation protects mice against a challenge with virulent malaria." Vaccine, 18(22): 2533-2540, 2000, incorporated herein in its entirety by this reference. Vaccination may be by single or multiple dose administration or via prime-boosting.

In a further embodiment the invention provides a method of eliciting an immune response in a subject said method comprising administering to a subject an immunologically effective amount of a composition comprising at least one antigen associated with microparticles, wherein the microparticles are in the same size range as viruses.

The subject may be any human or animal in which it is desired to elicit an immune response. This includes domestic animals, livestock (such as cattle, sheep, horses, cows, pigs, goats, llamas, poultry, ostriches, emus) and native and exotic animals, wild animals and feral animals.

The term "comprising" has the same meaning as given above.

An immunologically effective amount refers to an amount sufficient to generate an immune response in the subject, preferably after a single administration. This will vary depending on a number of factors including those discussed above, and may depend on whether the subject is a human or animal, its age, weight and so on.

The terms "antigen" and "associated with" have the same meanings as given above.

The term "immune response" refers to the cellular and humoral responses as described above, and also to the response by cells that assist in mounting or amplifying the immune response as described above. In particular the immune response may be provided by the proliferation and/or expansion of dendritic cells, particularly DEC205+, CD40+ and CD86+ cells.

The term microparticle has the same meaning as given above. Preferably the microparticle is between 0.03 and 0.5 µm, more preferably between about 0.03 and 0.15 µm, still more preferably between 0.03 and 0.1 µm. Even more preferably the microparticle is between about 0.03 µm and 0.05 µm, even more preferably between about 0.03 and 0.04 or between about 0.19 and 0.049 µm. Still more preferably the antigen/microparticle composition is particularly adapted to elicit a strong cellular and/or humoral immune response.

In a preferred embodiment the invention provides a method of eliciting an immune response in a subject said method comprising administering to a subject an immunologically effective amount of a composition comprising at least one antigen associated with microparticles, wherein the microparticles are in the same size range as viruses and the immune response comprises the stimulation and/or proliferation of dendritic cells. Preferably the microparticles are about 40 nm to 50 nm, most preferably 40 to 49 nm in size.

In another embodiment the invention provides a method of eliciting a protective immune response to an antigen via a single dose said method comprising administering, once only to a subject, an immunologically effective amount of a composition comprising at least one antigen associated with microparticles, wherein the microparticles are in the same size range as viruses and the immune response comprises the stimulation and/or proliferation of dendritic cells. Preferably the microparticles are about 40 nm to 50 nm, most preferably about 40 to 49 nm in size.

In another embodiment the invention provides a method of in vivo delivery of an antigen to dendritic cells in order to elicit an immune response said method comprising administering to a subject an immunologically effective amount of a composition comprising at least one antigen associated with microparticles, wherein the microparticles are in the same size range as viruses and the immune response comprises the stimulation and/or proliferation of dendritic cells. Preferably the microparticles are about 40 nm to 50 nm, most preferably about 40 to 49 nm in size.

The invention also extends to a method of producing an immunogenic microparticle/antigen composition comprising contacting microparticles which are in the same size range as viruses with one or more antigens such that the microparticles and antigens become associated. Those skilled in the art will be familiar with the techniques used to produce such a composition.

BRIEF DESCRIPTION OF THE DRAWINGS

The invention will now be described with reference to the following non-limiting examples and figures.

EXAMPLE 1

Materials and Methods Used

Mice and Immunizations

Figure 1:
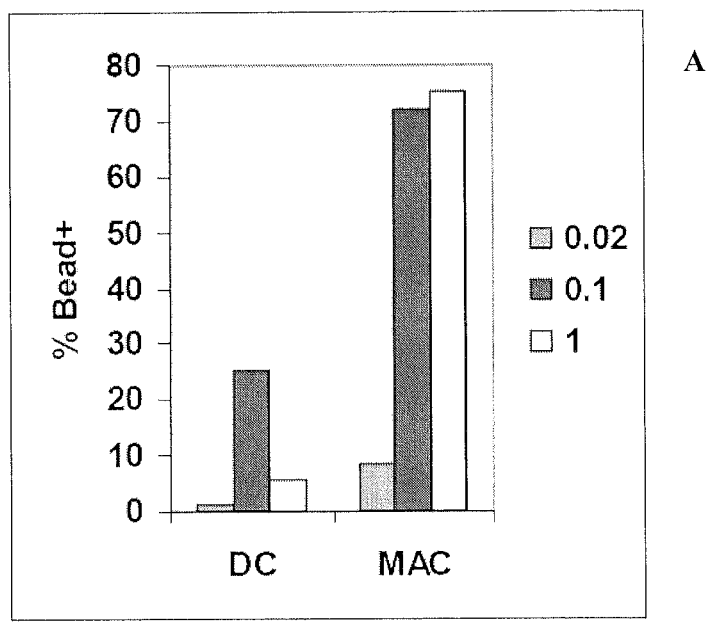
FIG. 1: Panel A—Differential uptake of particles of different sizes by macrophages compared to dendritic cells. 1000 fluorescent beads of 0.02, 0.1 or 1 micron size per cell were incubated overnight with cultured peritoneal exudate macrophages or bone marrow derived dendritic cells from C57BL/B6 mice and the percentage of fluorescent cells assessed by FACSCan. One of three similar experiments is shown. Similar differences in uptake of different bead sizes were obtained using 10 fold higher bead concentrations, a 3 hour pulse with beads or Balb/c derived antigen presenting cells. Panel B—Virus sized particles are preferentially found in lymph node cells in vivo. LEFT C57BL/B6 mice were inoculated intradermally in the footpad with 50 µl of 0.1% solution of fluorescent beads of different sizes (0.02, 0.04, 0.1, 0.2, 0.5, 1 and 2 micron) and the draining popliteal lymph nodes removed 10 days later to assess the percentage of cells that have taken up the beads by FACscan. The data is shown as mean percentage of fluorescent cells+/−Standard error (SE) of triplicate samples. The 0.04 and 0.1 micron particle sizes had significantly higher uptake to any other sized particles (p>0.001). In similar experiments using comparatively only 0.1 or 1 micron beads, 0.1 micron bead uptake was significantly higher than 1 micron in lymph nodes collected also at days 3, 6 or 9 after inoculation; Panels C & D—Virus sized particles are taken up preferentially by lymph node NLDC145+ (also known as DEC205+) (panel C) and F4/80+ (panel D) cells. Lymph node cells that have taken up fluorescent particles were assessed by FACScan analysis for co-expression of the dendritic cell marker NLDC145/DEC205 or the macrophage/monocyte marker F4/80. The data shows the percentage of NLDC145+ or F4/80+ cells that have become fluorescent due to bead uptake.
Figure 1:
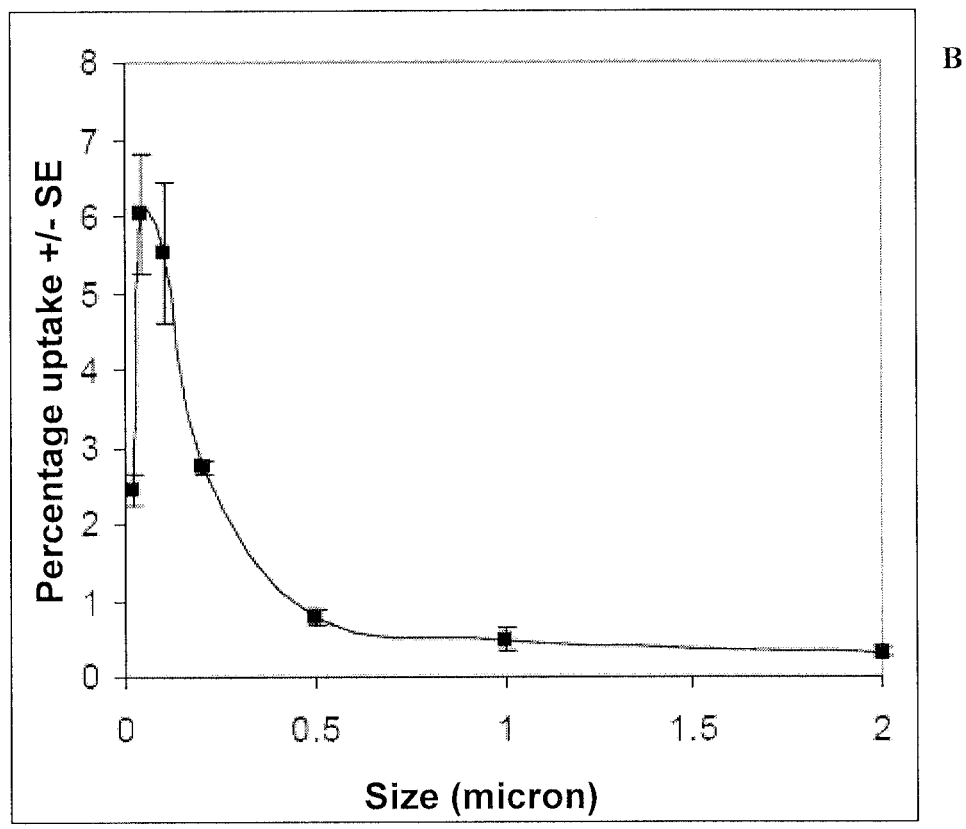
Figure 1:
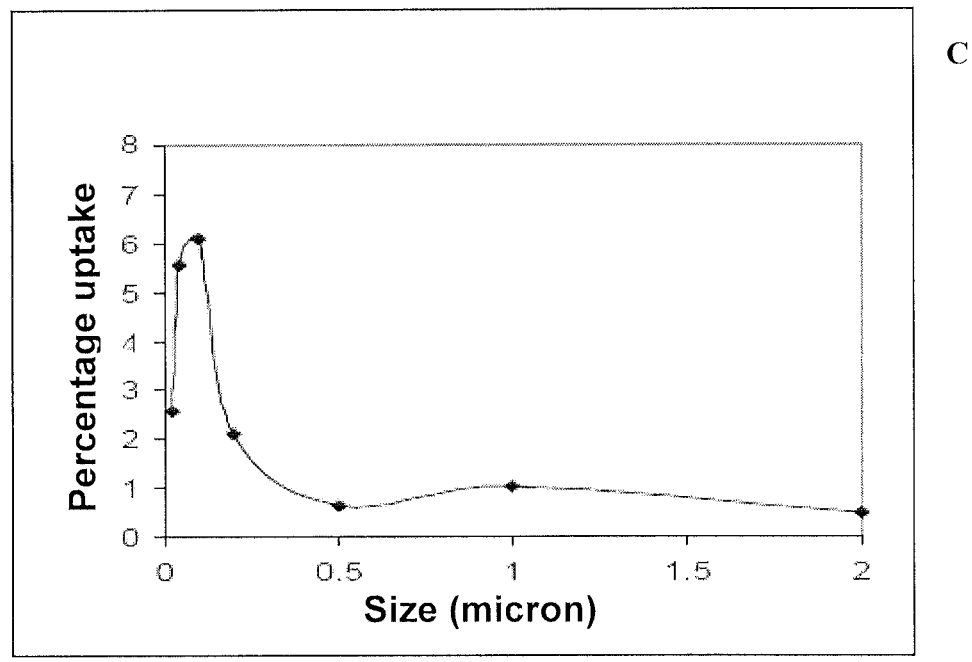
Figure 1:
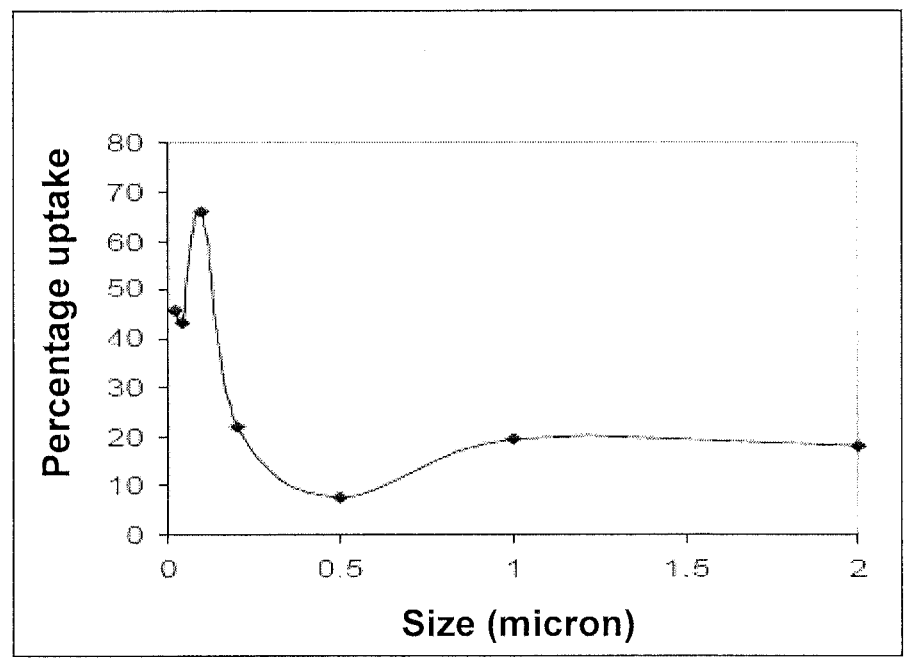

C57BL/6 and BALB/c 6- to 8-week-old mice were purchased from the Walter and Eliza Hall. Mice were immunized with 100 ml of antigen conjugated beads intradermally (ID) in the hind footpads.

Reagents:

All reagents including the antigen Ovalbumin (OVA, Grade III) and 1-Ethyl-3-(3-DimethylAminopropyl)Carbodiamide (EDAC) were purchased from Sigma unless otherwise stated. Monoclonal antibodies for FACScan and confocal studies were either purified in house from hybridoma lines on a Protein G column (Pharmacia) or purchased from Pharmigen. FITC conjugated and carboxylated fluospheres 0.02-2µ were purchased from Molecular Probes and non-fluorescent carboxylated microspheres from Polysciences. Abs to the following markers were used: MHC II, MHC I, CD11c, CD11b, F4/80, NLD-145, CD8alpha, CD40, CD80 and CD86. The anti-Rab4 monoclonal antibody used in confocal studies was the kind gift of Dr. Russel (Peter McCallum Research Institute).

Antigen Presenting Cells:

Denditric cells were prepared from bone marrow monocytes with minor modifications of previously published methods [5]. Briefly cells were harvested from tibia and long bones of the hind limbs by flushing out the cells from the bone cavities with media, following by red cells lysis. The cells were plated out at $1\times10^6$ cells/ml in RPMI ((CSL, AUST) supplemented with 10% heat inactivated foetal calf serum (FCS), 4 mM L-glutamine, 100 U/ml penicillin, 100 mg/ml streptomycin sulphate and 100 µM β-mercaptoethanol. and GM-CSF at 1000 units/ml and IL-4 at 0.2 ng/ml were added. The 10 ml cultures were grown for 5-6 days in petri-dishes of a 100 mm diameter at 37 C in a humid $CO_2$ incubator. Macrophages were recovered from the intraperitoneal (IP) cavity of mice three days after IP injection of thioglycollate, and cultured for 3 days to enrich for adherent cell fractions as described [6].

Bead-antigen conjugation was performed following the manufacturers instructions. Briefly, OVA was diluted to 2.0 mg/ml in 0.05M MES buffer pH 6.0 mixed in a volume ratio of 1:1 with beads of 2% solids/volume. The mixture was rocked gently for 15 minutes and then 4 mg/ml EDAC was added. The pH of the mixture was adjusted to 6.5 with dilute NaOH and the mixture was rocked gently for two to three hours. The reaction was stopped with glycine to a final concentration of 100 mM. After 30 minutes of mixing the preparation was dialysed overnight in the cold in PBS. The preparation was either used immediately or stored at 4° C. with 0.01% azide for later use.

Cytotoxicity Assays:

These were performed as described [3]. Briefly, effector cells for cytotoxicity assays were generated by culturing spleen cells for 7 days at $2.5\times10^6$/ml in 2 ml well plates at 37° C. in a humid $CO_2$ incubator with 10 µg/ml of the peptide antigen in RPMI medium (CSL, AUST) supplemented with 10% heat inactivated foetal calf serum (FCS), 4 mM L-glutamine, 100 U/ml penicillin, 100 mg/ml streptomycin sulphate and 100 µM βmercaptoethanol. Interleukin 2 (10 U/ml, recombinant human IL2, Lymphocult HT, Biotest, UK) was added on day 3. Targets were $^{51}Cr$ loaded EL4 cells, alone (background) or pre-pulsed for 1 h at 37° C. with 10 µg/ml of the SIINFEKL (SEQ ID NO:1) peptide or EG7 an ovalbumin transformed EL4 cell line. Unless otherwise stated assays were performed in duplicate at an effector:target ratio of 20:1. Spontaneous lysis (with media alone) and maximum lysis (with 5% triton) were set up for all targets in quadruplicate. Supernatants were harvested after 4 h. % Lysis was calculated as 100×((Experimental release–Spontaneous release)/(Maximum release–Spontaneous release). % Specific Lysis (% SL) was % Lysis with peptide–% Lysis with no peptide.

Cytotoxic T Cell Precursor (CTLp) Assays:

CTLp assays were performed as described previously [7] CTLp frequencies were determined from a minimum of 32 replicates, for at least 6 effector cell numbers ($1\times10^3$-$1.28\times10^5$). Cells were cultured in U-bottomed microtitre trays, with $5\times10^5$ mitomycin C treated syngeneic spleen cells, in DMEM supplemented with 10% fetal calf serum, 5 µM of SIINFEKL (SEQ ID NO:1) or OVA and 10 U/ml rhIL-2. Seven days later, each microculture was assayed for cytotoxicity by replacing 100 ml of culture medium with 100 µl target cell suspension containing $10^{4\,51}Cr$-labelled EL40R EG7 as targets. Cytotoxic activity was considered to be present if in each well $^{51}Cr$ release was found three standard deviations above the mean isotope release from 104 effectors cultured with stimulators only or from stimulator cells with peptide only or rIL2 only. A linear relationship ($0.987 \leq r2 \leq 1$) existed between the number of responder cells, represented on a linear scale, and the frequency of negative wells on a logarithmic scale. CTLp frequencies were determined as the inverse of responder cell dose required to generate 37% negative wells [8, 9]. CTLp frequency assays were performed three times and the individual frequencies did not differ by more than 20% from the mean value.

ELISPOT IFNγ Assays:

These were performed as described [3]. Briefly, 100 nl of $5\times10^6$/ml freshly isolated spleen cells were incubated with the stated stimuli for 18 hours on mixed acetate plates (MAHA Millipore) pre-coated with an anti-murine IFNγ mAb (R4), (EACC). Duplicate wells were set up for each condition. The media used was RPMI 1640 (CSL) supplemented as described above. After overnight incubation cells were washed off and the plates incubated with a second biotin conjugated mAb to murine IFNγ (XMG.21-biotin, Pharmigen, CA, USA), followed by an extravidin alkaline phosphatase (A-AP) conjugate at 1 µg/ml (Sigma). Spots of alkaline phosphatase activity were detected using a colorimetric AP detection kit (Biorad, Hercules, Calif., USA) and counted utilising a dissection microscope. The data are presented as spot forming units (sfu) per million cells. The SIINFEKL (SEQ ID NO:1) peptide was utilised at 2.5 µg/ml. Statistical analysis in protection studies the number of mice protected in each group was compared using a $\chi^2$ test in the Statcalc program in the EpiInfo Version 5.0 package. In immunogenicity studies the ELISPOT and Chromium release responses were compared between groups using the Student's t test with the Microsof Excel Version 5.0a package. Linear regression analysis was used to assess correlation between immunogenicity and protection using the SPSS for Windows statistical program package.

Bead Uptake by Dendritic Cells and Macrophages

Three day old macrophage cultures grown on microscope slides and five day old dendritic cell cultures were fed with different size fluorescent microbeads for periods of 5 minutes to 24 hrs. The cultures were then washed to remove free beads and prepared for FACScan or confocal analysis.

Analysis of Cells Taking Up Beads In Vivo:

Draining lymph nodes and spleens were collected from bead immunized mice at various time intervals from 12 hrs post immunization and up to 12 days. Cells were collected and after red blood cell lysis and washing they were prepared for FACscan or confocal analysis.

Cell Surface Marker Staining and Flow Cytometry:

For surface staining, $5 \times 10^5$ cells were incubated with PE-labelled MoAb to surface markers F4/80 and NLD-145, CD. In cases where the antibody was not directly labelled after two washing steps the cells were incubated with a second PE-labelled antibody specific for the first antibody. Naive serum of the species where the second antibody was raised was used in a blocking step before incubation with the second antibody. After two washes, the cells were washed with PBS/0.2% paraformaldehyde and analysed with a FACScan flow cytometer (Becton-Dickinson) and CellQuest software. Light scatter gates were set to exclude dead cells and nonlymphoid cells. Cells from bead immunized unstained for any surface marker and cells from naive mice stained with a PE-labelled antibody to a surface marker were used to determine compensation for overlap between the FITC and PE emission spectra.

Confocal Microscopy of Phagocytosed FITC-Labelled Beads:

An Olympus scanning confocal microscope was used with a Krypton-Argon laser source equipped with dual fluorescence and transmission detection to determine whether fluoresceinated beads of different sizes were phagocytosed by macrophages or dendritic cells. Serial sections through the samples were acquired at step sizes between 0.5-1.0 microns to determine phagocytosis and analysed on Optiscan Analyzer. Cells were excited at 488 nm and 568 nm for fluorescein and Alexa 594 respectively and detected through 530 nm and 610 nm band pass filters respectively. Throughout acquisition, laser power was kept below saturation levels and gain and offset parameters maintained within individual experiments.

ELISA Assays:

Antibody responses to OVA were measured using ELISA. Polyvinyl chloride microtitre plates were coated with OVA (10 μg/ml in 0.2 M NaHCO$_3$ buffer, pH 9.6) overnight at 4° C. The plates were washed 4× with PBS/0.05% Tween20 and 4× with PBS and then blocked for non-specific binding with 2% bovine serum albumin for 1 h at room temperature. After washing as above serial dilutions of the mouse sera were added and incubated for a further 1 h at room temperature. Non immune mouse serum was used as the negative control. The plates were washed and the bound antibody detected using horseradish-peroxidase-conjugated sheep anti-mouse Ig (Selinus, AUS) and the chromogenic substrate 2,2"-azino-di(3-ethylbenzthiazoline) sulphonate (Amersham, UK). The absorption at 405 nm was recorded using an EL 312e microplate reader.

EXAMPLE 2

Preferential Uptake of VSSP by Antigen Presenting Cells In Vitro and in Vivo

A number of studies using cells from the macrophage/monocyte lineage have shown particle size dependent phagocytosis, with optimal uptake at a 1 micron diameter [10, 11]. Uptake has been observed in dendritic cells, however, a comprehensive range of particle sizes has not been tested. The inventor was specifically interested to establish whether protein coated particles of viral size (0.03-0.1 μm), would be efficiently taken up by dendritic cells or macrophages. FIG. 1a shows that thioglycollate elicited peritoneal exudate macrophages internalised both 1 μm and 0.1 μm fluorescein-labelled particles (fluo-beads). Immature bone marrow derived dendritic cells, by contrast, were found to take in preferentially 0.1 μm sized fluo-beads. Confocal microscopy was used to confirm the particles were inside of the cells (not shown). This in vitro data suggested viral sized solid particles (VSSP) could also be preferentially taken up by antigen presenting cells in vivo. Fluorescent polysterene protein conjugated particles in a range of sizes (0.02, 0.04, 0.1, 0.2, 0.5, 1 and 2 μm) were injected intradermally (ID) into the footpad of C57BL/B6 mice and cells from the draining popliteal lymph nodes collected 10 days later for FACScan analysis. Particles of the 0.04-0.1 μm size were taken up preferentially by lymph node cells (FIG. 1b). Similar results were obtained analysing lymph node cells on days 1, 3, 6 and 10 after particle injection, and with unconjugated particles. VSSPs were efficiently taken up by antigen presenting cell expressing both macrophage and dendritic cell surface markers (FIG. 1b). Bone marrow derived dendritic cells in vitro also took up VSSPs. As expected, these cells were of a predominantly myeloid phenotype [12].

EXAMPLE 3

VSSP Prime High Precursor Frequencies of Cytotoxic and IFNγ Secreting T Cells as Well as Antibodies Efficient VSSP uptake by dendritic cells in vivo suggested their use for targeted antigen delivery and potential as novel vaccines. C57/BL mice were immunised with ovalbumin (OVA) coated particles of 0.02, 0.04, 0.1, 0.2, 0.5, 1 or 2 μm, boosted after 15 days and serum or spleen cells collected 10 days later. FIG. 2a shows optimal induction of IFNγ secreting CD8 T cell induction to the MHC class I restricted SIINFEKL (SEQ ID NO:1) epitope achieved using 0.04 μm sized particles. CD4 T cells responding to OVA were found at similar precursor frequencies with OVA conjugated particles ranging from 0.04-1 micron. Cytotoxic T cells to SIINFEKL (SEQ ID NO:1) were also induced with VSSPs and correlated with the precursor frequency of IFNγ secreting T cells ($R2=0.92$) (FIG. 2b). Surprisingly, OVA-specific IgG was also found at the highest precursor frequencies in mice immunised with 0.04 μm particles, followed by those immunised with 1 μm particles (FIG. 2c). Similar immunogenicity results were found with using VSSPs without fluorescein. Thus, in contrast to many immunogens and adjuvants promoting preferentially a cellular or a humoral response, VSSPs were capable of inducing high levels of both.

Figure 2:
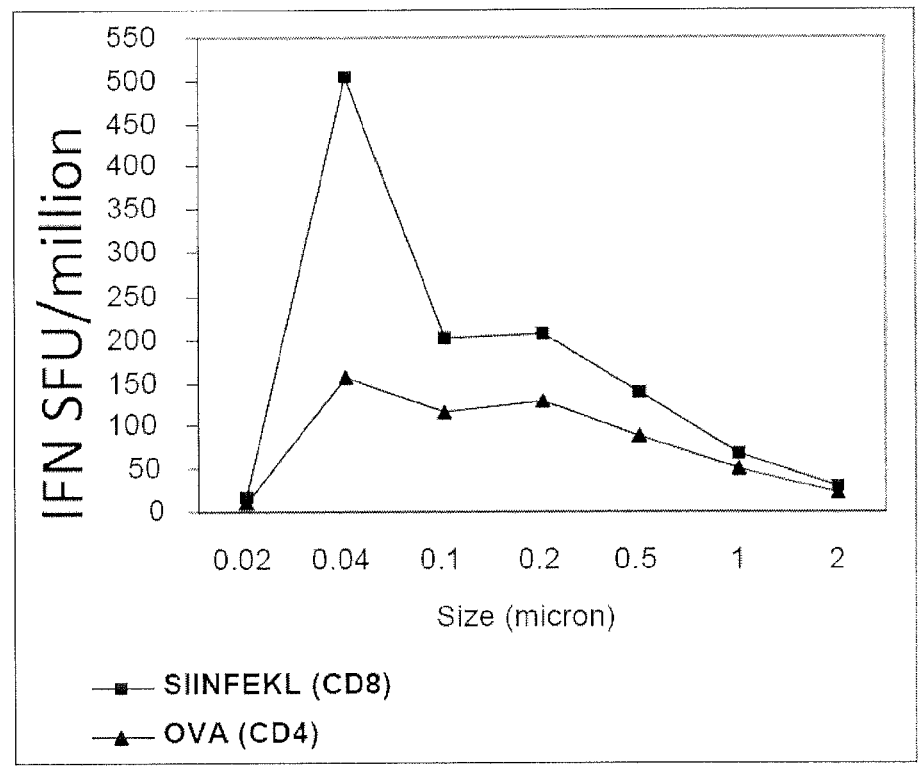
FIG. 2: Panel A—Induction of IFN γ producing CD8 and CD4 T cells by immunization with OVA conjugated to beads of different sizes. C57BL/B6 mice were immunised intradermally twice (10 days interval) with 100 µg of OVA conjugated to 0.02, 0.04, 0.1, 0.2, 0.5, 1 or 2 micron size beads and spleen T cell activity assessed 10 days after the booster immunisation by IFNγ ELISPOT. Responses were measured to the H-2 Kb restricted CD8 T cell epitope SIINFEKL (SEQ ID NO:1) or to whole OVA. In the case of assessing reactivity to OVA spleen cells were depleted from CD8 T cells before the assay with magnetic beads (Dynabeads) to quantify OVA reactive CD4 T cells. SIINFEKL (SEQ ID NO:1) was used at 2.5 µg/ml and OVA at 25 µg/ml. One of three similar experiments is shown. Two mice per group were immunized for each bead size. ELISPOT cultures were done in duplicates and average values of spot forming units (SFU) per million cells tested are shown. The standard deviation (SD) was always less than 20% of the mean. Panel B—Correlation between T cells with cytotoxic activity and IFNγ secreting T cells by ELISPOT in response to SIINFEKL (SEQ ID NO:1) C57BL/B6 mice were immunised with beads-OVA of different sizes and reactivity to SIINFEKL (SEQ ID NO:1) assessed by IFNγ ELISPOT as described above. In addition, the number of SIINFEKL (SEQ ID NO:1) specific T cells with cytotoxic activity was determined in parallel by limiting dilution analysis. Chromium loaded EL4 cells alone or pre-pulsed with 2.5 μg/ml of SIINFEKL (SEQ ID NO:1) were used as targets. The data shown illustrates the strong correlation (R square=0.9254) found between the two assays. One of two similar experiments is shown. PANEL C—Antibody production induced by immunisation with OVA conjugated to beads of different sizes. Serum was collected from the mice described in Panel A and serum dilutions tested for OVA specific IgG reactivity by ELISA. Individual mice receiving 0.02, 0.04, 0.1, 0.2, 0.5, 1 or 2 micron size OVA-bead immunisation are plotted. One of two similar experiments is shown.
Figure 2:
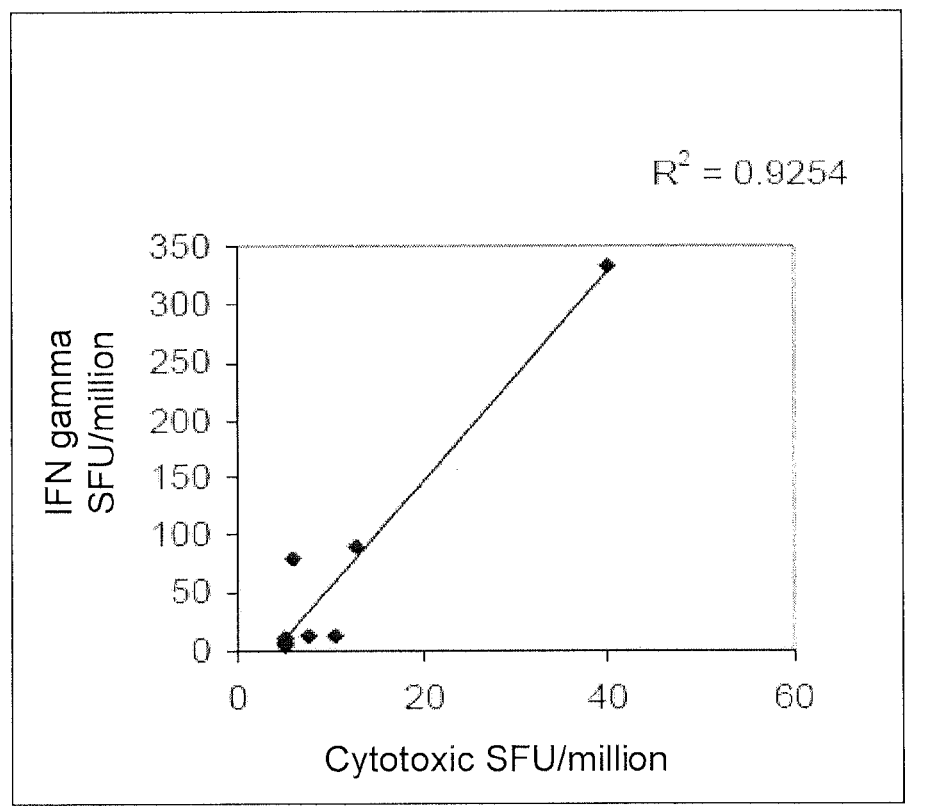
Figure 2:
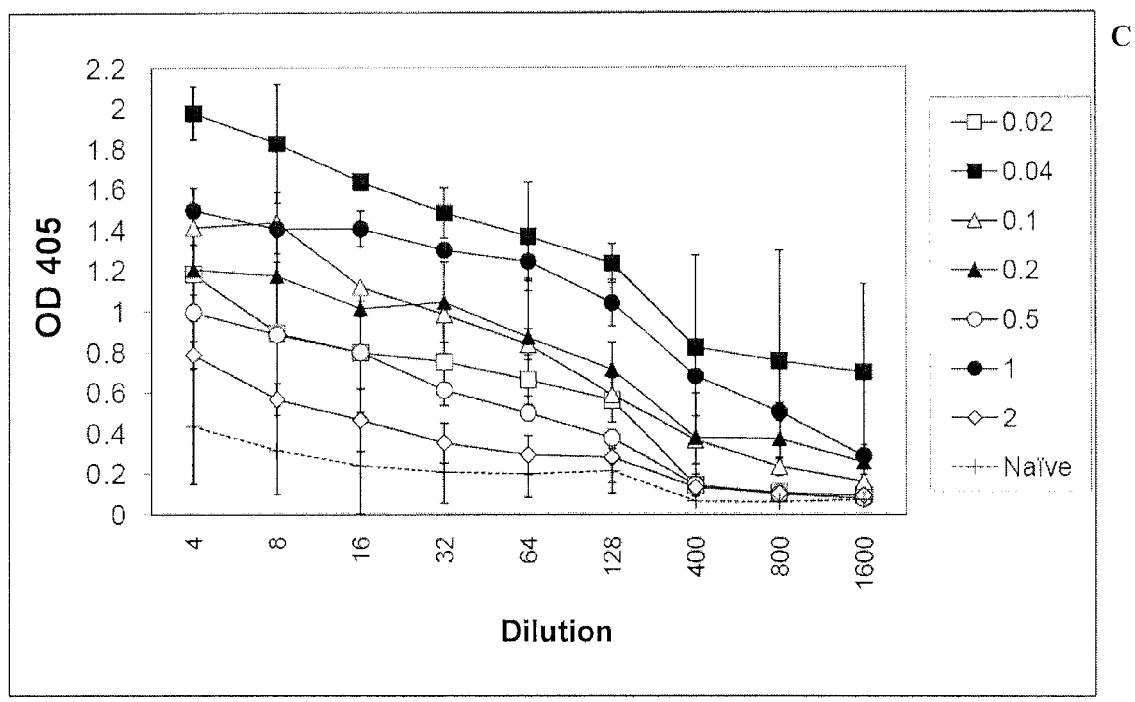
Figure 3:
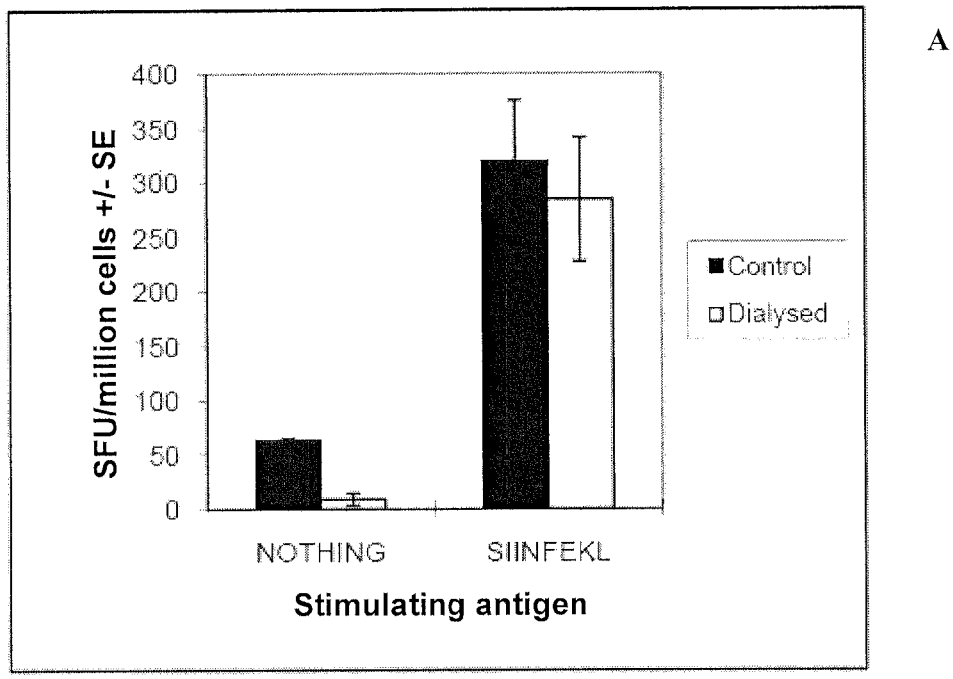
FIG. 3: Covalent conjugation of antigen to beads necessary to induce optimal T cell responses. Panel A—Bead-conjugated OVA alone accounts for MHC class I restricted T cell responses C57BL/B6 mice were immunized with OVA conjugated covalently to 0.04 micron beads without prior dialysis (Control) or following dialysis against PBS through a 300 Kd exclusion membrane (Dialysed). The induction of IFNγ producing splenic SIINFEKL (SEQ ID NO:1) specific CD8 T cells was assessed 10 days after one intradermal immunization by ELISPOT. The mean+/−SE for 4 mice per group assessed by ELISPOT in duplicate wells is shown. PANEL B—Co-administration of beads and soluble OVA is not sufficient to induce optimal MHC class I restricted T cells responses. C57BL/B6 mice were immunized with OVA conjugated covalently to 0.1 micron beads (Beads conjugated-OVA) or mixed with OVA prior to injection (Beads/OVA mixed). The induction of IFNγ producing splenic SIINFEKL (SEQ ID NO:1) specific CD8 T cells was assessed 10 days after one intradermal immunization by ELISPOT. The mean T cell precursor frequency for 2 mice per group assessed by ELISPOT in duplicate wells is shown.
Figure 3:
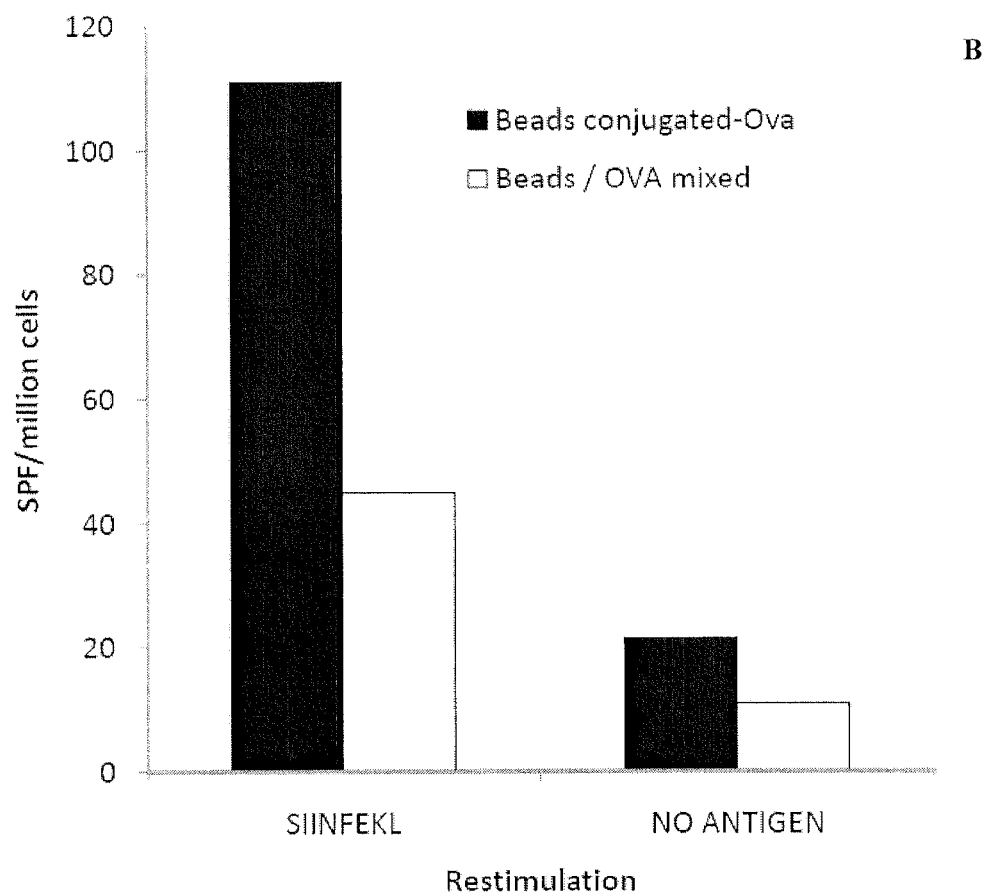

The results shown in FIG. 2 are based on injecting the same total amount of antigen after conjugation without eliminating residual soluble antigen. FIG. 3a shows that similar T cell responses were obtained with 0.04 micron VSSPs after the soluble antigen was eliminated by dialysis or ultracentrifugation. Therefore, there was no significant contribution from the soluble antigen to the observed T cell responses. This was further supported by the comparison of conjugated and unconjugated OVA and VSSP mixes. FIG. 3b shows that only covalently conjugated VSSP induced high levels of SIINFEKL (SEQ ID NO:1) specific T cells. Thus, covalent attachment to the VSSPs was necessary to target OVA into the class I presentation pathway and induce class I restricted T cells in vivo. It could be argued that a higher amount of conjugated protein in smaller compared to larger particles could by itself result in higher VSSP immunogenicity. However, this was not so, since: 1) Immunogenicity peaked at 0.04 μm and 0.02 μm sized beads induced little reactivity (FIG. 2), 2) 0.04-0.1 micron VSSPs were consistently more immunogenic than 1 μm particles independently of the level of antigen conjugation, (3) Increasing the immunising concentration of 1 μm particles up to 100 fold (up to 1 mg/mouse) over that used for VSSPs failed to enhance immunogenicity to the levels seen with a range concentrations of antigen conjugated to VSSPs, 4) Immunising with equivalent amounts of bound protein on beads of different sizes, or with the same number of different sized beads, consistently showed VSSPs to be more immunogenic than larger particles across a range of concentrations (0.5-1000 ug total OVA, 0.5-50 ug conjugated OVA and $10^3$-$10^8$ beads per animal).

EXAMPLE 4

A Novel Pathway for the Uptake and Processing of Particles

Figure 4:
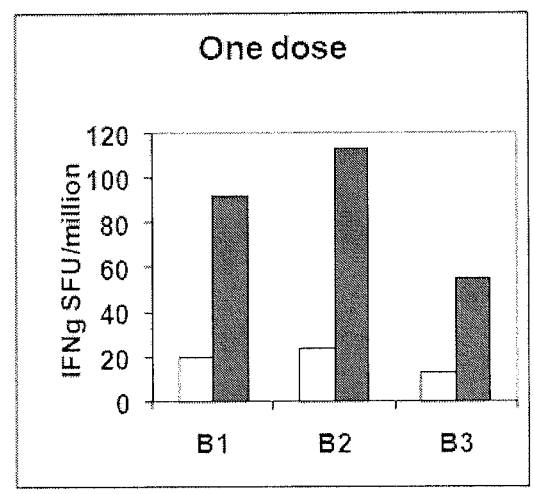
FIG. 4: A single immunization with viral sized beads-OVA is sufficient to induce long lasting high levels of MHC class I restricted T cells. Panel A—C57BL/B6 mice were immunized intradermally once, two or three times with beads-OVA (0.1 micron), each time 14 days apart and their IFNγ response to SIINFEKL (SEQ ID NO:1) examined in each case 10 days after the last immunization by ELISPOT. Three mice were immunised per group and the data shows the mean of duplicate assays on each mouse. One of two similar experiments is shown. Panel B—Mice were immunized once with beads—OVA (0.1 micron) and IFNγ responses to SIINFEKL (SEQ ID NO:1) or OVA tested by ELISPOT 12 or 82 days later. Antibody levels to OVA measured as in FIG. 2 were maintained at day 82.
Figure 4:
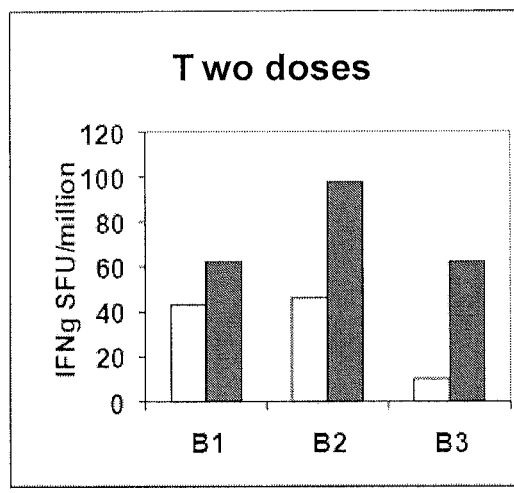
Figure 4:
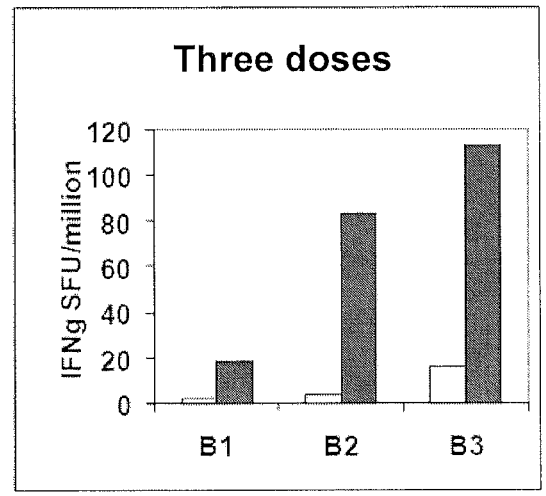
Figure 4:
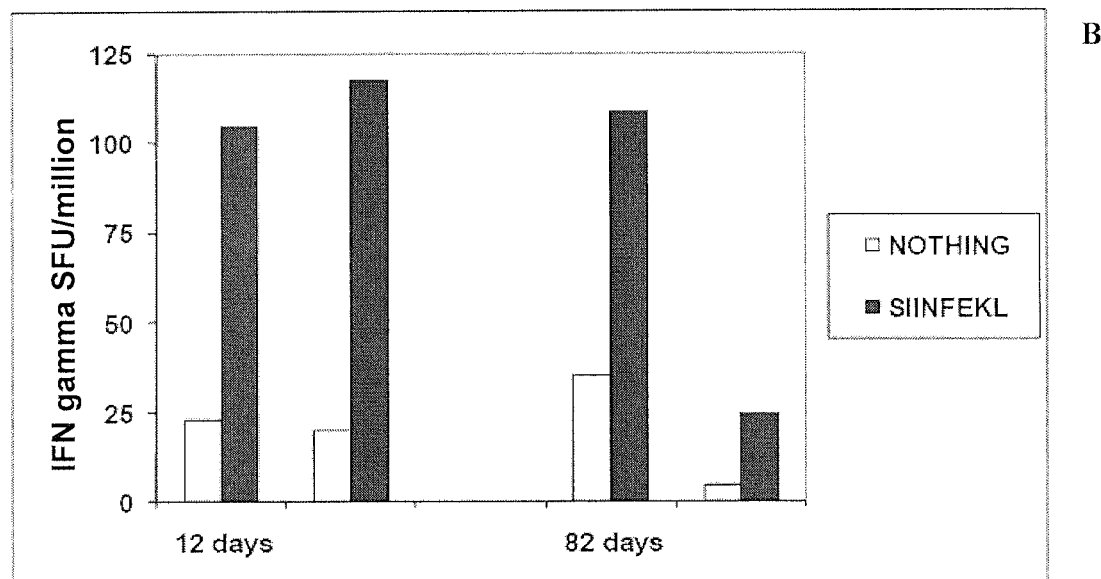

It has been suggested that peptides derived from digestion of exogenous antigen through the class II MHC processing pathway may be regurgitated and subsequently bind to empty class I MHC molecules at the cell surface [1, 10]. This alternative mechanism of class I presentation is independent of transport into the endoplasmic reticulum (ER) mediated by TAP (transporter associated with antigen processing). Hepatitis B surface protein VLPs are processed for class I presentation in macrophages by a TAP independent mechanism [2]. The inventor immunised TAP knockout C57/BL mice with OVA-conjugated VSSPs. No T cell responses above background levels could be detected to SIINFEKL (SEQ ID NO:1) or OVA in TAP-KO animals suggesting VSSP processing for class I presentation was by contrast, TAP dependent. A TAP dependent mechanism of class I presentation of exogenous antigen has been described for proteins adsorbed onto 1 μm particles based on 'leakiness' of endocytic vesicles and accidental release of antigen into the cytoplasm [1, 10]. Processing of such large particles taken up by phagocytosis involves an early conjugation step with lysosomes expressing the Rab4 adaptor protein [13]. The inventor used confocal microscopy to determine whether VSSPs would be routed via this pathway. FIG. 4 shows that Rab4 and VSSP fluo-bead containing vesicles did not co-localise either in bone marrow derived dendritic cells in culture, or in vivo in lymph node cells 24 hours after intradermal VSSP administration. VSSPs therefore may use a processing pathway which differs from that used by both VLPs or larger particles in that it is Rab4 independent and TAP dependent. The mechanism was further investigated in Example 7.

EXAMPLE 5

VSSP Induce Expansion of Antigen Presenting Cells In Vivo and In Vitro

C57BL/6 mice were left untreated (naïve) or immunized with fluorescent 0.1 μm fluo-beads intradermally in the foot pad. Popliteal lymph node (LN) were dissected 48 hours after injection and analysed for expression of CD40 by staining with PE conjugated antibodies specific for this marker.

Figure 5:
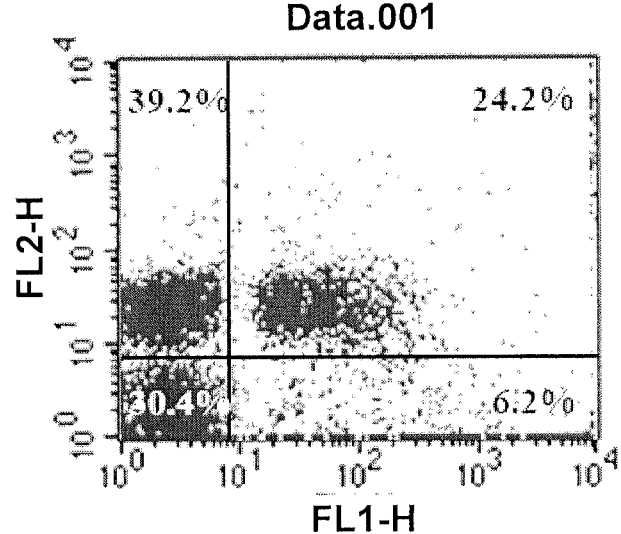
FIG. 5: Assessment of CD40 expression by cells that have taken up beads in the draining lymph node after intra-dermal immunization Popliteal LN cells from naive C57BL/6 mice (left) or mice immunized with fluorescent 0.04 μm fluo-beads intradermally in the footpad (right) were dissected 48 hours after injection and analysed for expression of CD40 by staining with PE conjugated antibodies specific to these markers. FL-1=FITC positive cells (bead+) and FL-2=PE positive cells (marker+). Background staining was negligible (<1%). The left panel represents popliteal LN cells from non-immunised animals, the right panel represents the same type of cells from VSP-OVA immunised animals.
Figure 5:
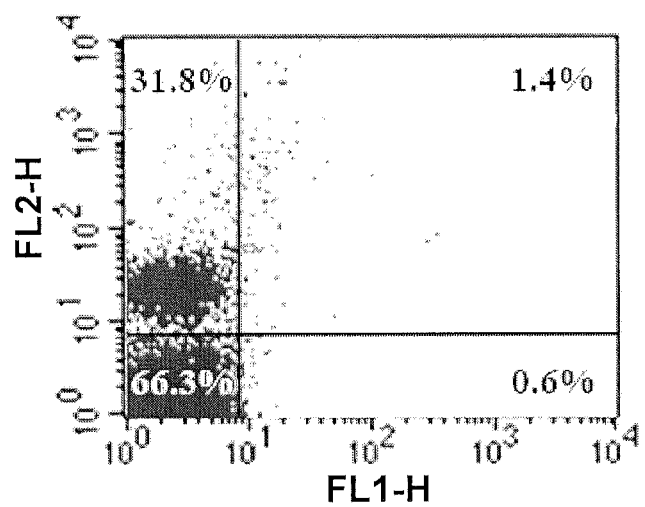

The results (FIG. 5) show that 0.04, 0.05 and 0.1 μm polystyrene beads alone or conjugated to OVA were able to increase up to 4 fold the total number of cells recovered from the draining popliteal lymph node after intradermal immunisation. Moreover, they caused 1.5 fold increase in the proportion of NLDC145+ (dendritic cell marker) but not F4/80+ (monocyte/macrophage marker) cells. They also enhanced >1.5 fold the proportion of lymph node cells expressing the activation molecules CD40 and CD86. FIG. 5 shows an example of the increase in CD40+ cells after immunisation observed by FACScan (33% to 63%). It also shows that many of these cells have taken up the 0.04 μm beads, in this case we used 0.04 μm beads with a fluorescent green core.

Figure 6:
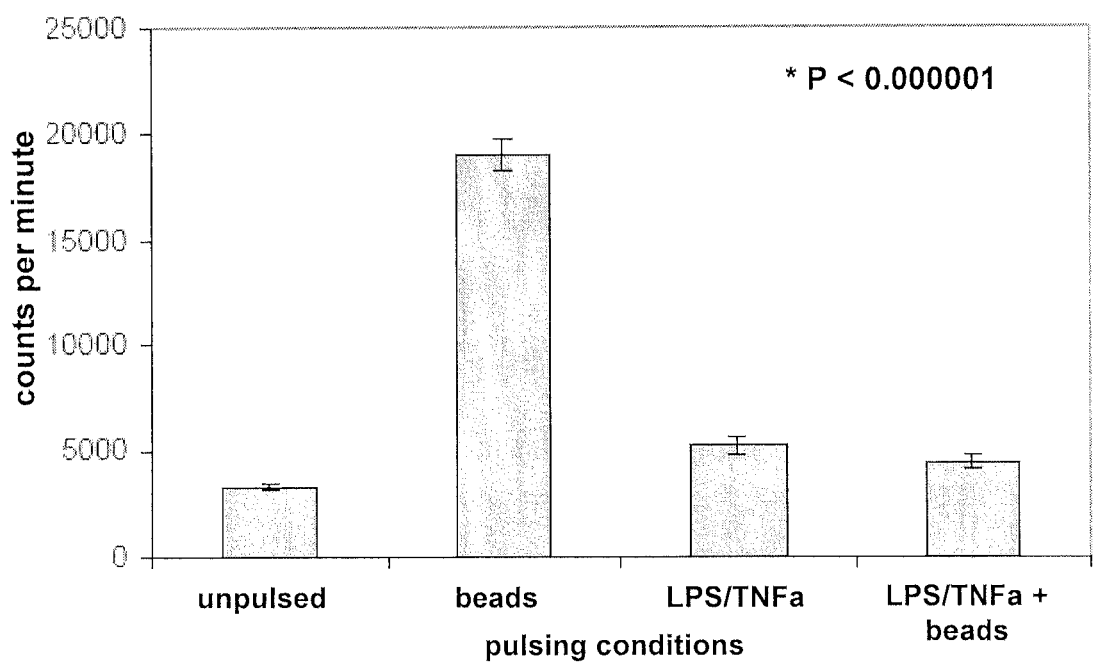
FIG. 6: Induction of immature and mature murine DC proliferation in response to 0.1 μm OVA-beads. DCs were cultured from bone marrow cells extracted from the tibia and femur of the hind legs of C57BL/6 mice, with the addition of GM-CSF and IL-4. After 5 days in culture, the cells were separated into the experimental conditions at $1.25 \times 10^6$ cells/1.25 ml and pulsed with conjugated beads to OVA (0.1 μm) at 1000 beads/cell. After 4 hours of pulsing, LPS and TNFα were added to appropriate cultures. The cells continued to incubate overnight, and proliferation thymidine assay set up the next day and incubated overnight. Each value represents triplicate averages±SD (*$p<0.00001$ between unpulsed DCs and experimental groups, unpaired t-test).

0.04, 0.05 μm and 0.1 polystyrene beads alone or conjugated to OVA were able to induce dendritic cells purified from mouse bone marrow to proliferation in vitro. Immature, but not mature (after activation with LPS and TFN-alpha) dendritic cells were susceptible to this activating effect of VSSP (FIG. 6).

These data together suggest that particles of 0.04-0.1 μm in size (VSSP) have the unsuspected and previously unknown ability to stimulate antigen presenting cells, including dendritic cells, and specifically cells expressing potent co-stimulatory molecules like CD40 and CD86 to proliferate and expand. This could further explain why they are so potent. Moreover, it suggests a mechanism by which VSSP may have an adjuvant effect (see Example 14 below) even for responses to antigen when it is not chemically conjugated to them.

EXAMPLE 6

Extended Phenotype of Cells Taking Up VSSP Rapidly after Injection

Figure 7:
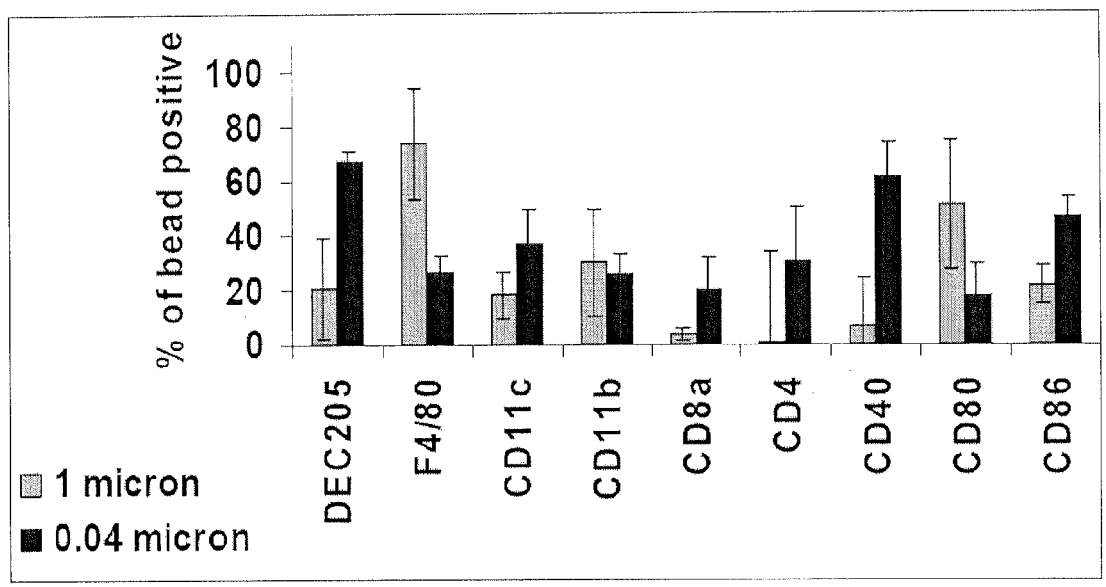
FIG. 7: Phenotypic characterisation of APC taking up 0.04 compared to 1 μm particles in vivo C57/B6 mice were injected in the footpad with 50 μl of 0.04 or 1 μm fluobeads-OVA. Draining popliteal LN were analysed 48 hours later for co-staining of bead positive cells with cell markers of activation and antigen presenting cell lineage, the mean+/−SE for 3-14 mice/marker is shown. 0.04 and 1 μm fluobead+ cells had significantly different expression of DEC205, F4/80, CD40, CD80 and CD86 ($p<0.05$).

To assess further which cells take up VSSP rapidly after intradermal footpad injection (and thus may be responsible for subsequent activation of immunity), the draining popliteal draining lymph node was dissected. The phenotype of cells that had taken up 0.04 μm VSSP-OVA with a fluorescent core was then analysed by FACScan and compared to identical particles but which were 1 μm in size. FIG. 7 shows the proportion of 0.04 μm bead+ or 1 μm bead+ cells expressing each phenotypic marker. Cells taking up 0.04 μm beads were mostly NLDC145+, CD40+ and CD86+. In addition more CD11c+, CD4+ and CD8+ cells were 0.04 than 1 μm bead+. This highly activated DC phenotype of cells that have taken up 0.04 μm beads may further explain why the immune responses we observed are so potent, particularly CD8 T cell responses.

EXAMPLE 7

Uptake and Processing of Microparticles

To address the mechanism of 0.04 μm bead-OVA uptake by dendritic cells (DC), bone-marrow derived DC were incubated with inhibitors of phagocytosis (cytochalasin D, CDD); clathrin pit (amiloride, AML) or caveole mediated internalisation (phorbol myristate acetate, PMA) [14, 15]. DC were cultured in triplicate with PMA, AML, CDD, filipin (FIL) or ammonium chloride (AM) (all from Sigma) at the stated concentrations for 30 min. OVA-fluorescent 0.04 μm beads were added for a further 3 hours and uptake was quantified by FACScan.

Figure 8:
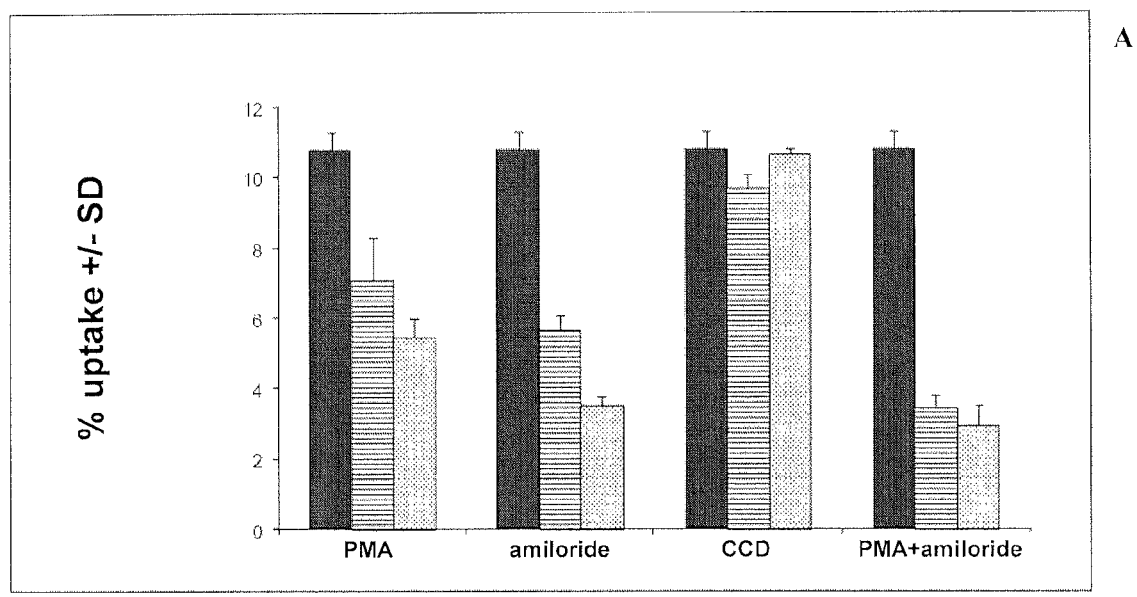
FIG. 8A: Mechanism of viral size particle uptake by DC. Bone marrow derived cultured DC were incubated with phrobol myristate acetate (PMA) at 0 (black), 5 (white), 10 μM (grey); amiloride (AML) at 0 (black), 1 (white), 3 mM (grey) (white), or cytochalasin D (CDD) at 0 (black), 0.25 (white) or 0.5 μg/ml (grey) for 30 min and 0.04 μm-OVA-fluorescent particles added a further 3 hours. Selective inhibition of caveolae, clathrin coated pit formation, or phagocytosis has been reported for 10 μM PMA, 3 mM amiloride and 0.5 μg/ml CCD, respectively 14, 15. When used together PMA was kept constant at 10 μM and AML was added at 1 (white) or 3 mM (grey). The number of fluorescent cells was assessed by FACScan. Data is presented as the mean+/−SD of triplicate cultures.
FIG. 8B: Confirmation of the mechanism of uptake DC were incubated with nothing, CDD 1 μg/ml, filipin (FIL) at 1 μg/ml or ammonium chloride (AC) at 40 mM for 30 min and 0.04 μm or 1 μm fluorescent beads added a further 3 hours. Selective inhibition of caveolae or clathrin coated pit formation has been reported for 1 μg/ml filipin and 40 mM ammonium chloride, respectively 14-17, 29. The number of fluorescent cells was assessed by FACScan. Data is presented as the mean+/−SD of triplicate cultures.
Figure 8:
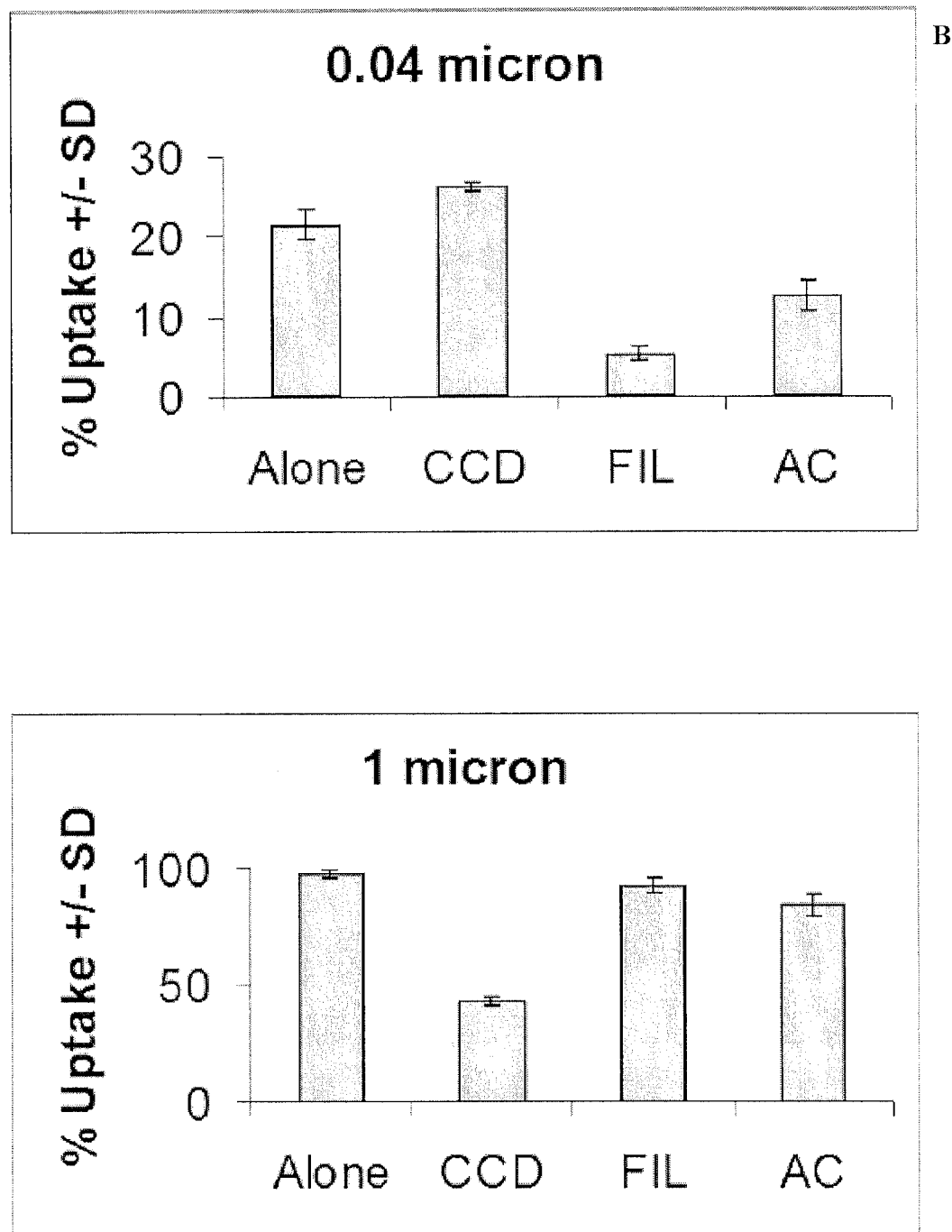

PMA and AML both decreased 0.04 μm beads-OVA uptake by DC, whereas CCD failed to cause any inhibition (FIG. 8a)

Inhibition by PMA and AML was additive (FIG. 8a). This suggested clathrin pits and caveole could both be involved in VSSP uptake.

Amiloride acts by inhibiting Na+-H+ exchange necessary for receptor mediated endocytosis [14]. The inventor tested additionally ammonium chloride which inhibits the assembly of clathrin pits by interfering with cytosol acidification [14]. Ammonium chloride inhibited uptake of 0.04 but not of 1 μm size beads (FIG. 8b), confirming a role for clathrin pits in VSSP uptake. Caveole have been suggested to mediate a novel mechanism for uptake of viral particles in DC [15]. The inventor results using PMA suggest that caveole were involved in VSSP uptake in DC (FIG. 8a). To confirm this, the inventor used another inhibitor of caveole, filipin. Filipin acts through cholesterol sequestration, whereas PMA affects the phosphorylation events regulating caveole internalisation [14, 15, 16, 17]. Similarly to PMA, filipin blocked 0.04 μm but not 1 μm bead uptake, confirming the inventor's hypothesis (FIG. 8b).

Caveole and clathrin pits can convey molecules to endosomal and lysosomal compartments [14, 16]. Alternatively, caveole may deliver antigen directly into the cytosol [17] leading to cytoplasmic processing and TAP dependent transport into the endoplasmic reticulum for presentation with MHC class I [1, 18].

These results, together with those shown in Example 4, indicate a novel pathway for processing of antigens presented in accordance with the present invention. The immunogenic composition of the invention appears to be taken up by antigen presenting cells via caveole and/or clathrin pits, after which the antigens are processed by Rab4 independent and TAP dependent pathways for MHC class I presentation. This observation is novel in that the ability of caveole to induce the TAP-dependent antigen processing pathway and CD8 cells has not been reported before.

EXAMPLE 8

Figure 9:
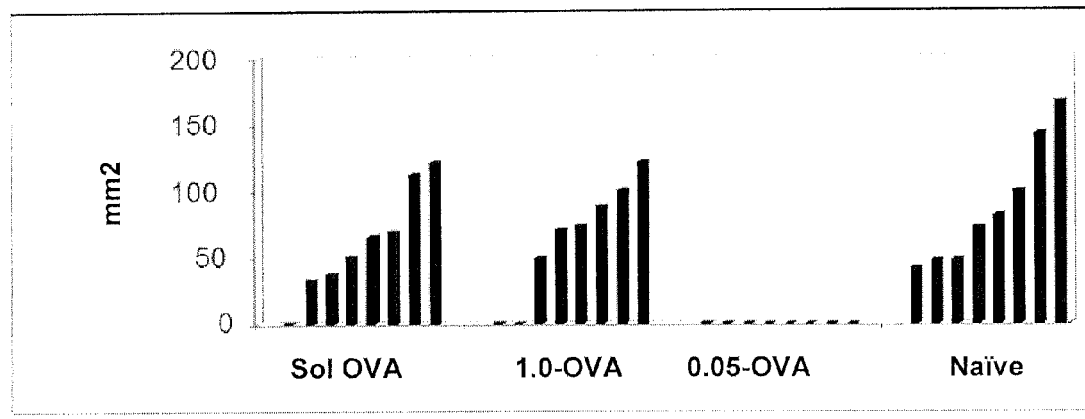
FIG. 9: Soluble OVA and 1 μm-OVA beads fail to induce comparable protection to 0.05 um-OVA beads. C57/B6 mice were immunised ID with OVA conjugated to 0.05 um or 1 um beads, soluble OVA or left untreated and then challenged as above. Data is presented as the individual tumour sizes at day 10 for 8 animals in each group. One of two similar experiments is shown. The difference in the frequency of tumours between the 0.05 um-OVA bead group and each one of the other groups was significant: $P=0.0001$ vs. naïve; $p=0.0007$ vs. soluble and $p=0.0035$ vs. 1 um bead-OVA.

Comparison of Protective Efficacy 50 nm (i.e. 0.05 μm) (VSSP) OVA conjugated particles were compared directly with OVA alone or 1000 nm (i.e. 1 μm) OVA conjugated particles, for ability to protect mice against subsequent subcutaneous challenge with 100,000 tumour cells (EL4) expressing OVA. All mice were immunised with 100 μg of either of the above (or nothing=naïve) intra-dermally once and then challenged with tumour 30 days later. FIG. 9a shows that VSSP-OVA prevented completely the growth of OVA expressing tumours, whereas OVA alone or with 1000 nm beads had a non-significant effect on protection.

EXAMPLE 9

Figure 10:
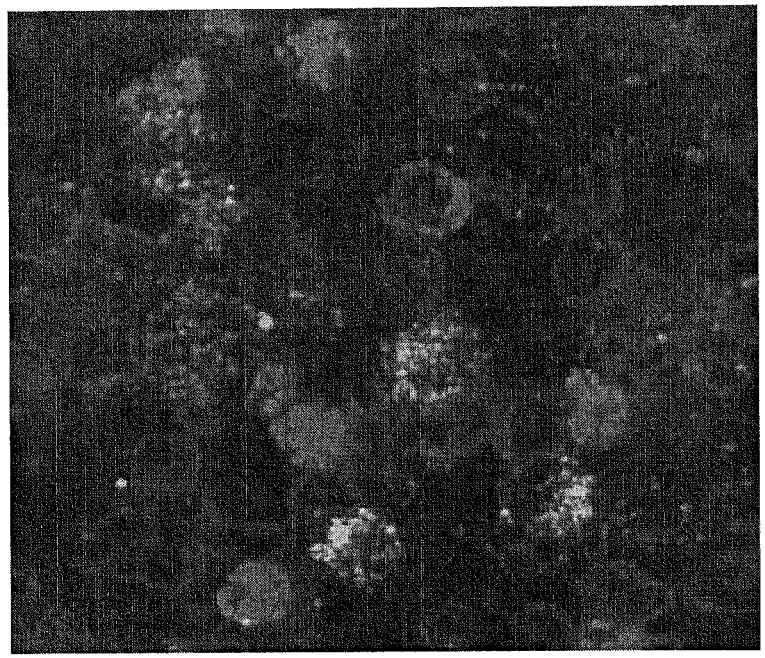
FIG. 10: Viral sized particles do not co-localize with early endosomes (LEFT). Bone marrow derived DC were incubated overnight with 0.1 micron beads-OVA (500 beads/cell), washed gently to remove free beads and prepared for confocal microscopy by spinning onto glass slides. Cells were then fixed in paraformaldehyde, permeabilised with triton and stained the presence of the early endosomal marker Rab4 using a biotin conjugated monoclonal antibody followed by streptavidin-Alexa. Similar results were observed with unconjugated 0.04 and 0.1 micron beads and one of three experiments is shown. Fluorescent 0.1 micron beads similarly failed to co-localise with Rab4 staining using DC incubated with beads for 30 minutes or for 3 hours. (RIGHT) Mice were injected intradermally in the hind footpad with 0.1 micron beads-OVA and the draining popliteal lymph nodes dissected 48 hours later for confocal analysis as described above. No co-localization was observed for the Rab4 marker and OVA conjugated or unconjugated 0.1 micron or 0.04 micron beads. One of three experiments is shown. By contrast co-localization was confirmed for the positive control mice immunized with 1 micron sized fluorescent beads.
Figure 10:
Figure 16:
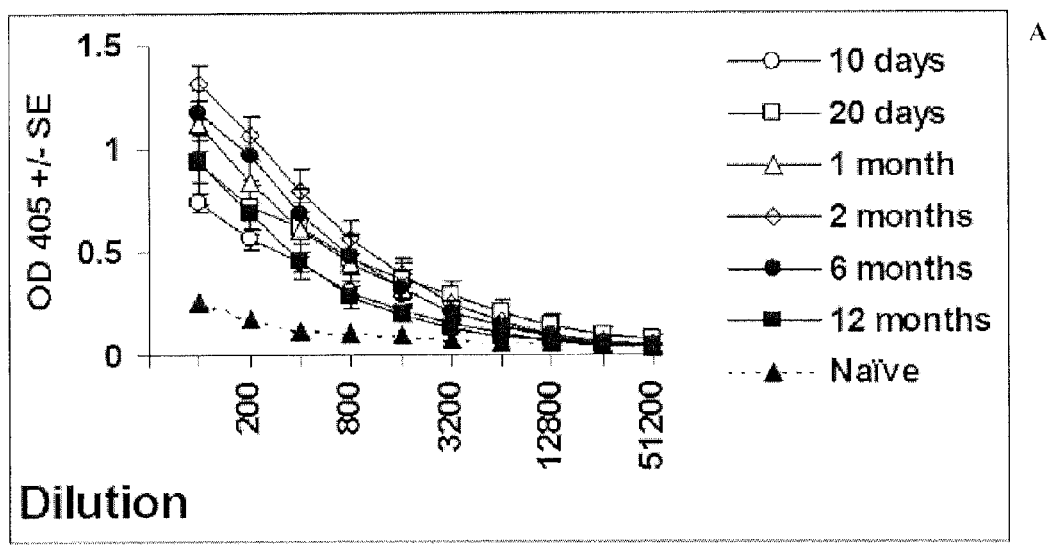
FIG. 16: PANEL A Induction of long lasting antibody responses by a single immunisation. C57/B6 mice were immunised once with OVA conjugated to 0.04 µm beads and sera collected at different time-points. The mean optical density at 405 nm+/−SE for each group of four animals in OVA specific IgG ELISA is shown. Naïve sera is shown as negative control. One of two similar experiments is shown. Similar ELISA results were obtained for total Ig and no IgM or IgA was detected (not shown). OVA alone failed to induce IgG responses over PBS immunised animals and OVA in Complete Freunds Adjuvant (CFA) induced IgG responses a log higher than single dose 0.05 µm beads-OVA (not shown). PANEL B Induction of long lasting high levels of IFNγ □ producing T-cells by a single immunisation with 0.04 µm beads OVA C57/B6 mice were immunised ID once with OVA conjugated to 0.04 µm beads (black or chequered bar), soluble OVA in PBS (white bar) or with OVA mixed in with 0.04 µm beads (grey bar). Precursor frequency of SIINFEKL (SEQ ID NO:1) reactive spleen T-cells was assessed 10 days later (back, white and grey bars) or 12 months later (chequered bar) by IFNγ ELISPOT. Four mice were tested per group and one of two similar experiments is shown. Average values of spot forming units (SFU) per million cells+/−standard deviation (SE) are shown for each group. In similar experiments using 10 times less antigen (10 µg VSP-OVA) a single immunisation induced 102+/±56 SIINFEKL (SEQ ID NO:1) specific spleen cells per million (n=4). Cytotoxic T-cell responses in standard Chromium release assays were also observed 10 days after a single immunisation (>50% Specific lysis for 3/3 animals at E:T ratio 20:1; not shown).
Figure 16:
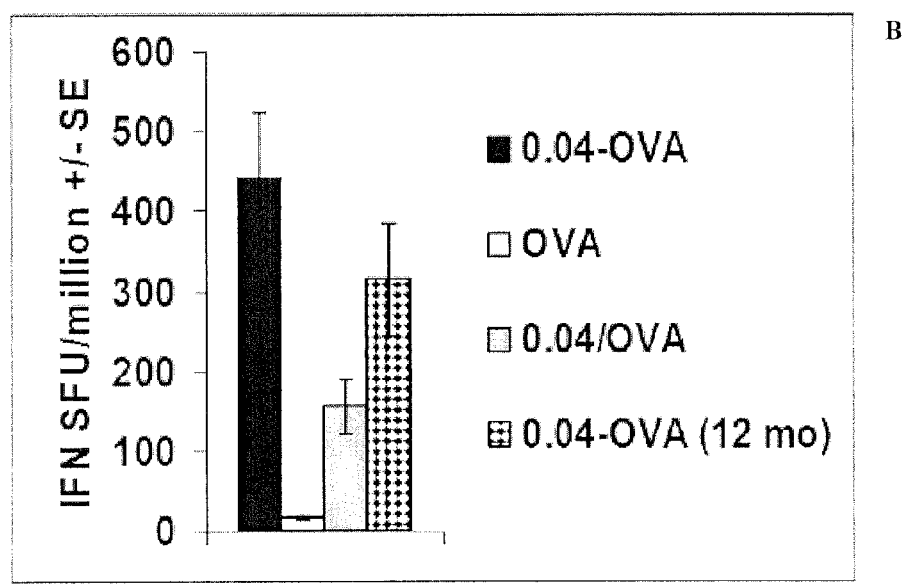

A Single VSSP Immunization Induces High Levels of Immunity and Protects Against Tumor Challenge Intradermal immunisation with OVA-conjugated VSSPs induced IFNγ producing and cytotoxic SIINFEKL (SEQ ID NO:1) specific T cells (FIG. 10a and 1a and b). Additional immunizations did not further increase reactivity (FIGS. 10b and 10c). T cells could be maintained at high precursor frequencies 82 days after immunization (FIG. 10d). Antibody responses were similarly maintained (FIG. 16). The CD8 T cell precursor frequency levels achieved by a single VSSP immunization were higher than those observed for single, or even multiple doses of VLP particles and are only comparable to the highly efficient heterologous prime/boost regimes [1, 2, 3, 19, 20]. High IFNγ producing and cytotoxic T cell precursor frequencies are associated with protection against many intracellular pathogens and cancer [21, 22, 23]. The inventor immunised C57/BL mice with a single intradermal dose of OVA-conjugated VSSPs and then challenged them with the EG7 tumor cell line, which expresses cytoplasmic OVA and is a target for cytotoxic SIINFEKL (SEQ ID NO:1) specific T cells in vitro. The results show that VSSP immunised mice were completely protected against tumor challenge, whereas all the naïve controls developed tumors. In addition, antibody levels were also increased following a single administration of antigen conjugated VSSP, similarly to those observed in FIG. 2c.

Further Work on VSSP Vaccines

Examples 10 to 13 described below formally demonstrate that VSSP can be used with a variety of antigens and induce broad immunity comprising both IFN and IL4 producing T cells. High levels of IgG, but not the potentially allergenic IgE antibodies are also induced after a single dose.

The effectiveness of VSSP for therapy is shown in an additional two models. 1) 100% clearance of established tumours (see Example 10) and 2) protection against lethal malaria after a single administration of the vaccine (see Example 11). This further confirms VSSP as an unusually potent and flexible vaccination protocol to develop single dose vaccines against a variety of diseases. Moreover, on the basis of these findings the inventor believes that VSSP may be used for therapy as well as prevention of cancer.

EXAMPLE 10

Clearance of Established Tumours

The inventor has observed that a single immunisation with beads-OVA protects completely against subsequent challenge with tumours expressing OVA.

C57/B6 mice were immunised once with 100 μg bead (0.05 μm)-OVA (ID) or left untreated (naïve). After 30 days, mice were challenged with 5×10$^6$ EG7 tumour cell lines. Tumour size was measured using calipers on days 3-13 after immunisation. For regression studies, mice were given the EG7 cells and eight days later divided into groups of similar tumour size distribution. One group was left untreated and the other was immunised with bead-OVA after 3 days (ie day 11 after administration of tumour cell line).

Figure 11:
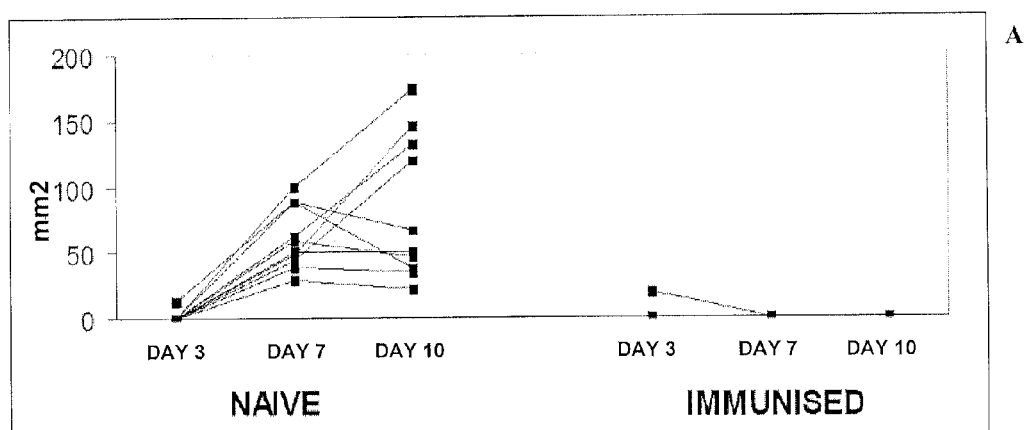
FIG. 11: Protection against tumour PANEL A C57/B6 mice immunised intradermally (ID) once with OVA-VSSP (immunised) or left untreated (naïve) were challenged 30 days later subcutaneously with 5×10⁶ EG7 (tumour cells). Tumours were measured using calipers. Individual tumour growth curves for 10 animals per group are shown. PANEL B Tumours were induced as above and at day 8 of tumour growth (day 0 of immunisation) 6 animals left untreated (Naïve) and 6 immunised ID with OVA-VSSP (Immunised). Individual growth curves are shown day 3-13 after immunisation.
Figure 11:
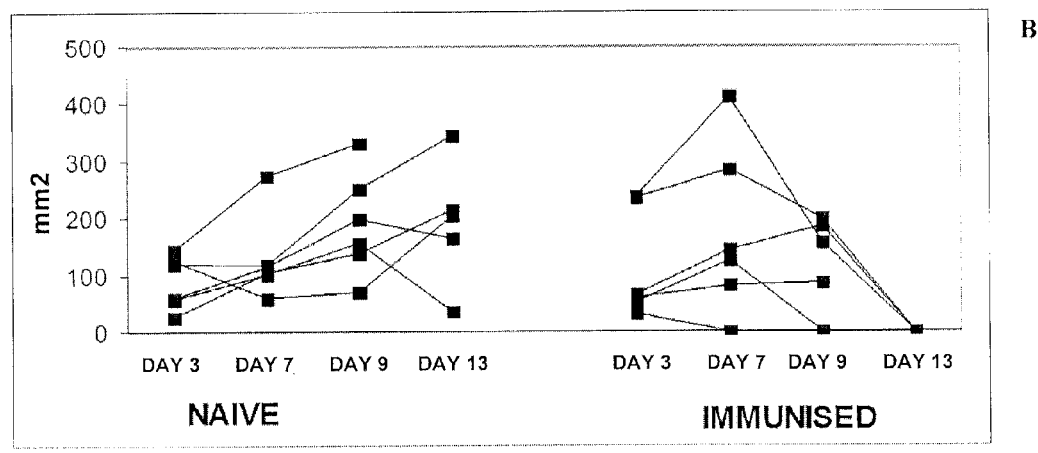

The inventor now shows that already established tumours can be cured by a single immunisation into a tumour bearing mouse. Tumours were cleared from immunised mice within two weeks after a single injection. This therapeutic ability is highly unusual for any cancer vaccine, and makes this vaccination vehicle highly promising for development of a therapeutic vaccine (FIG. 11B).

Mucin-1 or Muc1 is a breast cancer associated antigen. Immunisation once with VSSP-Muc1 protein also inhibited tumour formation in mice challenged with tumour cell lines expressing the breast cancer antigen (see FIG. 11A).

EXAMPLE 11

Protection Against Malaria

The inventor demonstrates that polysterene beads of 0.05 μm in diameter may be used as a vehicle to induce protection against malaria in mice. A lysate from *Plasmodium yoelii* infected red cells was conjugated to beads and used to immunise mice which were then challenged with a lethal dose of the parasites.

Blood was collected from C57BL/6 mice infected with *P. yoelii* 17XL at 50% parasitaemia. Red blood cells (RBC) recovered after centrifugation 800 g for 15 min were freeze/thawed three times and sonicated (lysate). Lysate was conjugated to 0.05 μm particles as described above. Beads-lysate, beads-OVA or lysate alone were injected ID. Immunised or naïve C57BL/6 mice were challenged two weeks later intra-peritoneally with 1,000,000 *P. yoelii* 17XL infected RBC.

Figure 12:
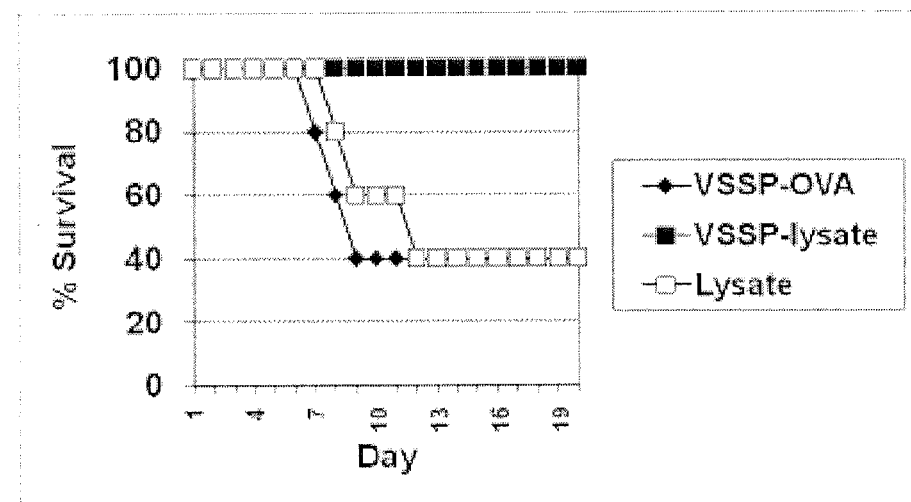
FIG. 12: Survival of mice to lethal malaria challenge after VSSP immunisation. C57/B6 mice immunised intradermally once with 100 µg of VSSP-OVA, VSSP-lysate or lysate alone were challenged with 500,000 lethal *Plasmodium yoelii* 17XL infected C57/B6 red-blood cells. Survival was monitored daily. 5 animals were challenged per group and one of six representative experiments is shown. In similar experiments naïve mice had 40% survival after 2 weeks (8/20 mice). The lysate was generated by repeated freeze-thaw of *P. yoelii* 17XL infected red-cells and ultra centrifugation and conjugated to VSP using the standard protocol.

All the animals survived the challenge, whereas 60% of the animals immunised with the lysate alone (without bead conjugation) failed to control the infection and died (FIG. 12). This is the first demonstration of a single dose vaccine being able to confer protection against blood-stage malaria. A single dose vaccine particularly attractive for malaria and other diseases present extensively in the Third world, since it simplifies administration and distribution of the vaccine, ensuring wide population coverage.

EXAMPLE 12

Cellular Immunity

Figure 13:
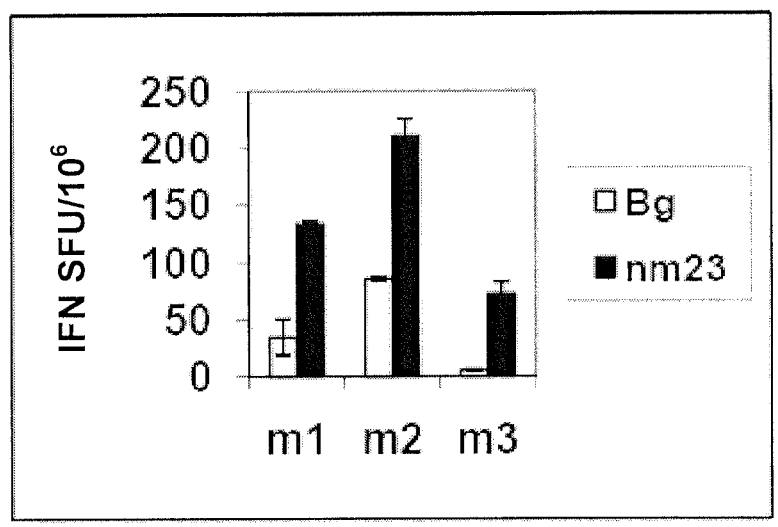
FIG. 13: The antigen nm23 was conjugated to 0.05µ bead (VSP) as described before for the antigen OVA, injected intradermally into mice at 100 µg/mouse and 10 days later IFN gamma reactivity assessed in the spleens of immunised animals by ELISPOT. The data id presented as the precursor frequency of cells responding to nm23 per million spleen cells as spot forming units (SFU/million)±the standard deviation of the mean (SD). The individual responses of three mice (m1-m3) are shown.

1) Polysterene beads of 0.05 μm in diameter conjugated to antigens other than OVA, such as the cancer antigen nm23 also induce strong cellular immunity as evidenced by the induction of high levels of IFN gamma secreting T cells (FIG. 13).

Figure 14:
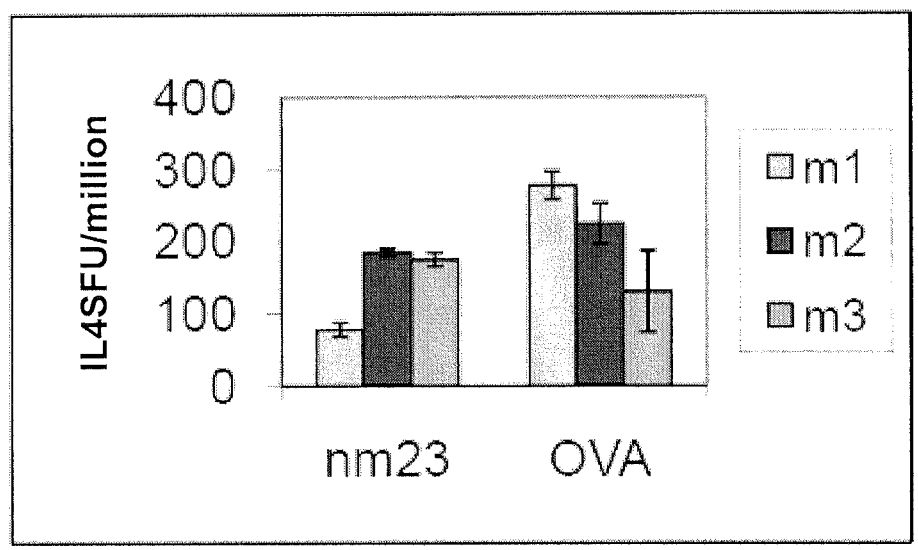
FIG. 14: The cancer antigen nm23 or OVA were conjugated to VSP per standard protocol and 100 µg/mouse injected intradermally. 10 days later the induction of IL4 secreting cells was assessed by ELISPOT. Data is presented as SFU/million+/−SD for three individual mice immunised with each immunogen.

2) As well as inducing cellular immunity, beads-OVA or beads-nm23 induced high levels of IL4 (FIG. 14). This lymphokine promotes the production of antibodies, which may explain why we observe good antibody induction as well as cellular immunity (which requires IFN gamma) was observed.

EXAMPLE 13

Antibody Immunity

Figure 15:
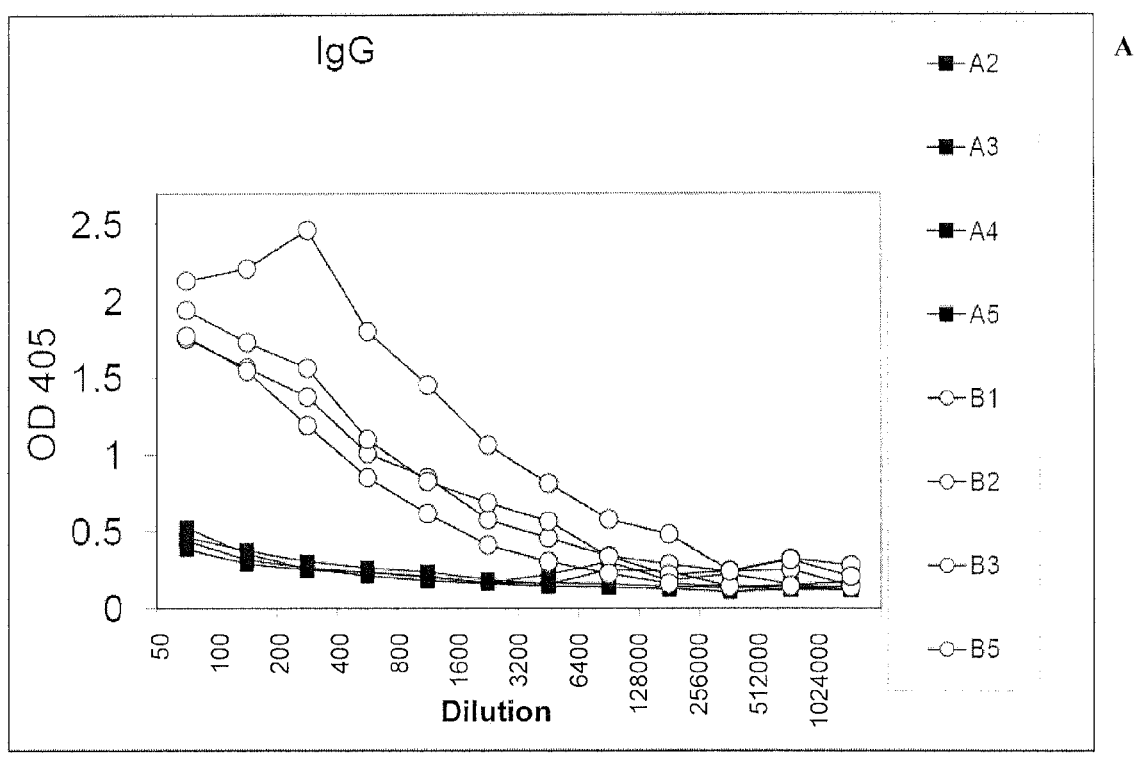
FIG. 15A: Antibody reactivity to OVA in the sera of mice immunised once intradermally with 0.05 µm beads conjugated to OVA (VSP-OVA) and assessed 90 days later by ELISA (B group) in comparison to non-immunised controls (A group).
FIG. 15B: The same sera from mice in FIG. 15A was tested for the presence of OVA specific IgE antibodies by ELISA, in two naïve mice (A2 and A3) and three VSP-OVA mice (B2, 3 and 5).
Figure 15:
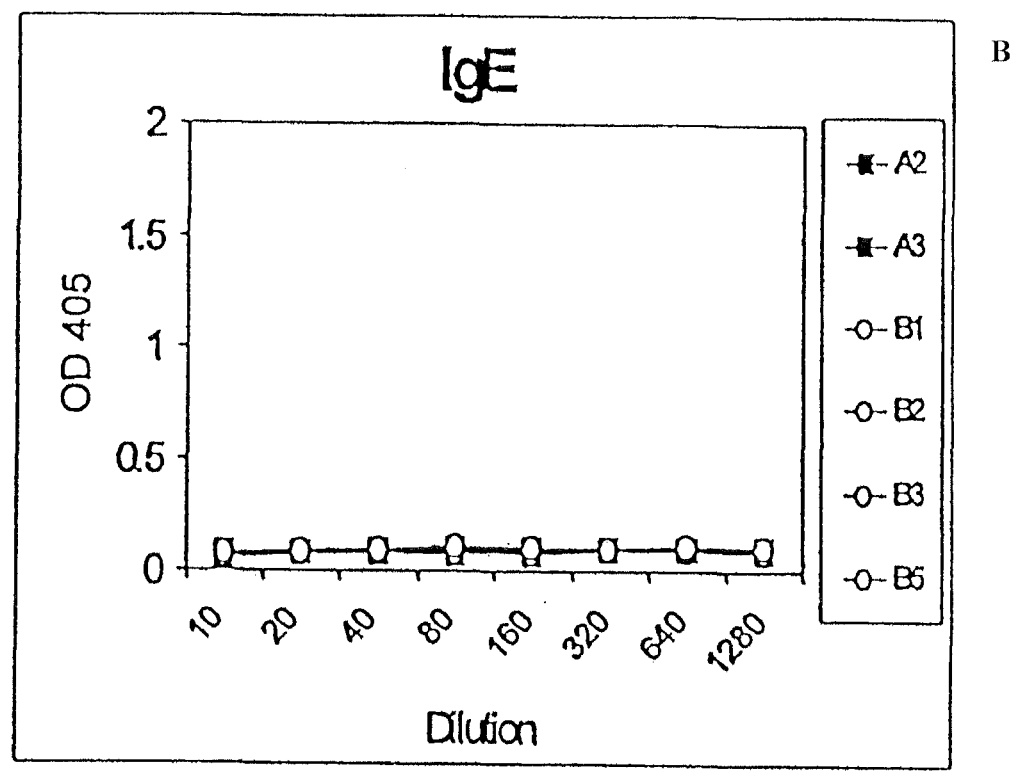

1) Polysterene bead of 0.05 μm in diameter conjugated to OVA induced, after a single intradermal (ID) injection induced high titres of IgG antibody (FIG. 15A).

2) Despite high IgG levels, there are no detectable IgE levels. Therefore, this vaccine is demonstrated formally to have no risk of inducing potentially damaging (since they are involved in allergy) IgE responses (FIG. 15B).

EXAMPLE 14

Administration Via Different Routes and Induction of IgG and IgA Antibodies

With a view to identifying useful routes of administration of the vaccine in humans, as well as intra-dermally as described above, VSSP conjugated to OVA (100 μg/mouse) was administered to mice intra-peritoneally, sub-cutaneously, intra-nasally and intra-rectally. 3-4 mice per group were tested 30 days after a single immunisation. Similarly to the intra-dermal, all routes induced T cells which secreted IFNg to SIINFEKL (SEQ ID NO:1) or to OVA by ELISPOT assay (1/50,000 to 1/2,000 spleen cells). Surprisingly, in contrast to the initial observations using intradermal injection which induced high levels of IgG but little or no IgA, VSSP-OVA by these other routes induced serum IgA responses, and the intra-rectal and intra-nasal route did not induce detectable IgG (titre<1/100) (Table 1). VSSP by the intra-rectal, intra-peritoneal, intra-nasal and subcutaneous routes could therefore also be used to induce protective immunity to diseases where IgA plays a protective role, such as mucosal infections (eg. in lung, cervix or gut).

TABLE 1

| Route | Serum IgG titre | Serum IgA titre |
| --- | --- | --- |
| Intra-rectal | <1/100, <1/100, <1/100 | 1/1280, 1/640, 1/1280 |
| Intra-peritoneal | 1/1640, 1/100, 1/400 | >1/5120, >1/5120, >1,5120 |
| Intra-nasal | <1/100, <1/100, <1/100, <1/100 | 1/160, 1/320, 1/320, 1/640 |
| subcutaneous | 1/800, 1/200, 1/6560 | >1/5120, >1/5120, >1/5120 |

Unusually High IgG Responses After Two Doses

Immunisation twice with VSSP-OVA (100 μg/mouse 14 days apart) led to the generation of surprisingly high serum Ig and IgG antibody titres of >1/500,000 as assessed by ELISA. Similar results were obtained for specific IgG antibodies after two immunisations with the breast cancer antigen nm23 and the malaria antigen MSP4/5, when conjugated to VSSP.

EXAMPLE 15

Long-Lasting Responses

Responses to VSSP-OVA were surprisingly long-lasting. FIG. 16 shows that strong IgG OVA specific antibody by ELISA (Panel A) and CD8 T cell responses to SIINFEKL (SEQ ID NO:1) by IFNg ELISPOT (Panel B) present one year after a single intradermal immunisation (100 μg/mouse). Panel B shows in addition that antigen has to be covalently conjugated to the solid particle for optimal immunogenicity.

EXAMPLE 16

Heterologous Prime-Boost

Figure 17:
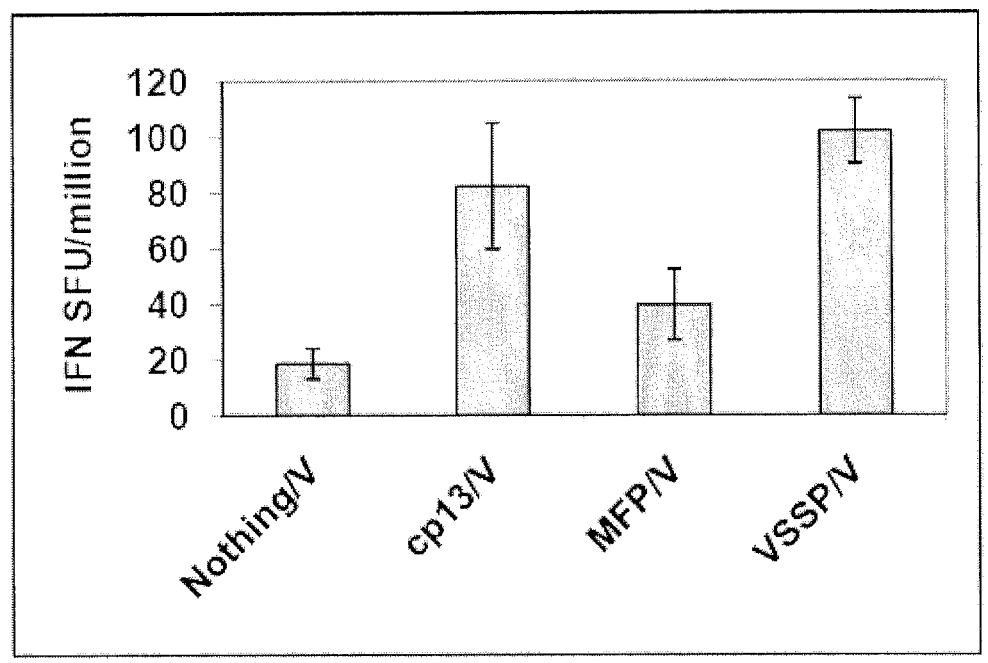
FIG. 17: Prime/boost C57/B6 animals were left untreated (Nothing) or primed intradermally with 100 ug of peptide cp13-32 from MUC1 conjugated to 700 ug of KLH in Complete Freunds Adjuvant (cp13), mannan conjugated recombinant MUC1-GST fusion protein (MFP) or 0.1 um VSP conjugated to MUC1-GST fusion protein (VSP). 14 days later animals were boosted intradermally with a million infectious vaccinia virus expressing the MUC1 protein, and reactivity to the epitopes in cp13-32 assessed by IFNg ELISPOT 10 days later. The data shown is the mean number of IFNg producing cells+/−SE per million spleen cells averaged for 2-3 animals/group.

Vaccinia-MUC1 was used to boost responses of animals primed with nothing, peptide cp13-32 (cp13) from MUC1 in complete Freund's Adjuvant (CFA), Mannan conjugated MUC1 (recombinant MUC1-GST fusion protein) (M-FP) or 0.1 μm VSSP-MUC1 (recombinant MUC1-GST fusion protein) (VSSP). FIG. 17 shows responses to the peptide 13-32 region of MUC1 were enhanced in the VSSP-MUC1 primed, Vaccina-MUC1 boosted group compared to animals that received Vaccinia MUC1 alone (Nothing/V compared to VSSP/V). Therefore VSSP-antigen would be suitable for use in heterologous Prime-boost protocols.

EXAMPLE 17

Material Composition of the Solid Core for VSSP

Figure 18:
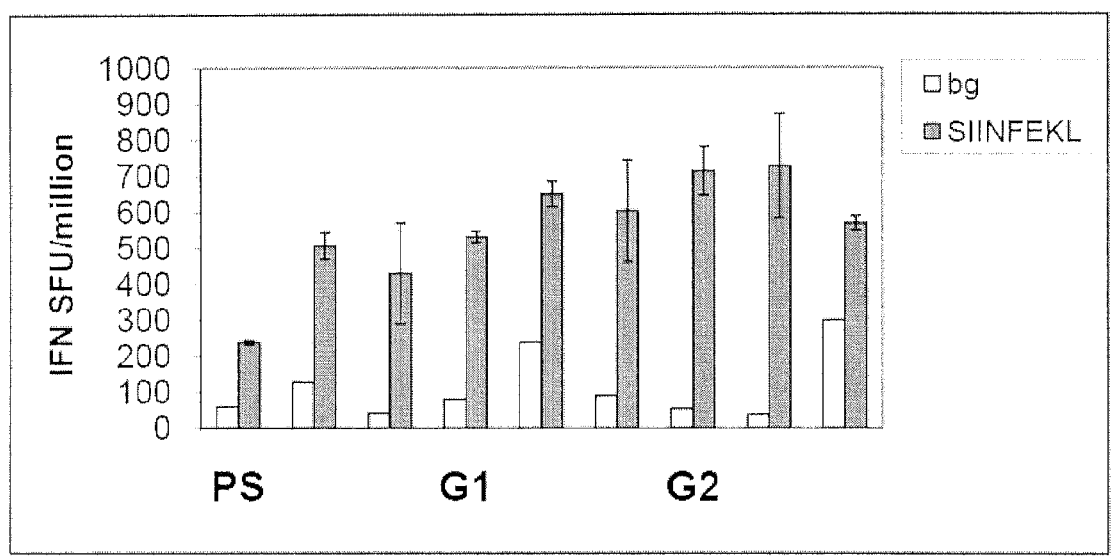
FIG. 18: Comparison of polystyrene and glass 0.05 µm VSP-OVA particles. Polystyrene 0.05 µm beads were conjugated to OVA as before (PS) and compared to OVA conjugated glass beads in the same way (G1). In addition, a different chemical procedure was compared for the glass beads. Briefly, glass beads were weighed and suspended to 2.5% solids in PBS and washed twice. PBS was removed by 5 minute centrifugation in a microfuge. The bead pellet was resuspended in 8% gluteraldehyde in PBS ph 7.4 and mixed gently at room temperature overnight. The beads were then washed 3× with PBS resuspended in PBS and 500 µg of protein per ml was added and mixed gently for 5 hours. The beads were then pelleted and the reaction was stopped by resuspending the pellet in 0.5 M ethanolamine and mixing for 30 minutes. The beads were then washed in PBS and used for immunization (G2). Polystyrene (PS) or glass (G1 or G2) VSP-OVA were immunised intradermally at 100/µg/mouse and SIINFEKL (SEQ ID NO:1) specific IFNg secreting T cells quantified 10 days later from spleens by ELISPOT. The data shows individual mean+/−SE for three animals per group.

The inventor's hypothesis that the 0.04-0.05 μm size of solid core is the principal determinant of VSSP immunogenicity predicts that particles made of material other than polystyrene would be highly immunogenic within this size range. Thus, she compared immunogenicity in mice after a single immunisation intradermally with 0.05 μm particles made of polystyrene (PS) or of glass (G1 or G2) and conjugated to OVA using the same chemical procedure (G1) or binding using glutaraldehyde (G2). FIG. 18 shows that VSSP made of either polystyrene or glass were similarly highly immunogenic inducing a high precursor frequency of IFNg producing T cells to SIINFEKL (SEQ ID NO:1) by ELISPOT. Therefore, the solid core of VSSP for protein conjugation can be provided by glass as well as polystyrene, and it is anticipated that other materials for the solid core will also be functional, for example PLG.

EXAMPLE 18

Conjugation of Antigen to VSSP

Figure 19:
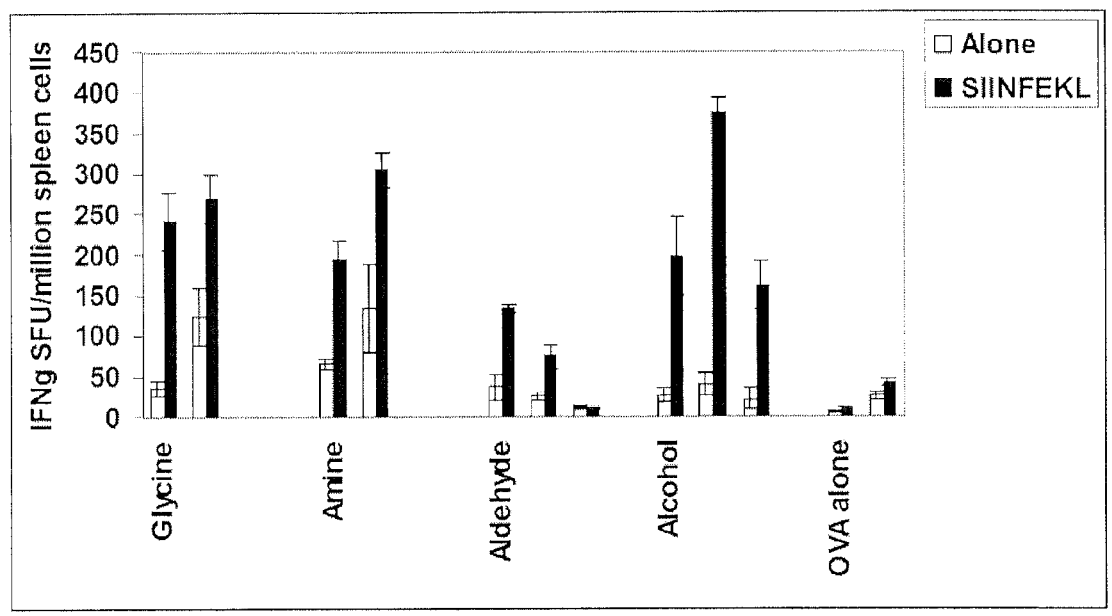
FIG. 19: Mode of bead conjugation and immunogenicity. Ovalbumin at 2 mg/ml in 50 mM MES buffer (ph 6.0) was mixed with the polystyrene carboxy modified 0.05 µm beads (2% solids) for 15 minutes. 1-ethyl-3-(3-dimethylaminopropyl)-carbodiiamide was added to each preparation at 4 mg/ml (pH 6.5) and incubated at room temperature for 2 hours. The standard (Glycine) was quenched with 7 mg/ml of glycine or 20 µl of 1 M ethanolamine (amine) pH 7.4, or 20 µl of 1 M aminoacetaldehyde dimethyl acetal (aldehyde) pH 8.0, or 20 µl of 1 M ethylenediammne (alcohol) pH 7.4. The preparations were incubated at room temperature for approximately 16 hours. All the preparations were dialysed overnight in PBS at 4° C. The aldehyde preparation was quenched further with 20 µl of 1 M HCL and incubated for 4 hours, and dialysed overnight in PBS at 4° C. 2-3 C57/B6 mice were immunised with 100 ug intradermally of each one of these VSSP-OVA particles and immunogenicity assessed in spleens by IFNg ELISPOT to the CD8 T cell epitope SIINFEKL (SEQ ID NO:1). Results are shown as mean+/–SE of SFU/million spleen cells for each animal.

The results show that mixing antigen with 0.05 µm particles makes it more immunogenic than antigen alone, but that covalent linkage is necessary for optimal immunogenicity. The chemical procedure used to conjugate antigen to VSSP could therefore theoretically be a determinant of immunogenicity. Specifically the overall charge of the particle could promote interaction with specific serum or other endogenous proteins. These in turn could theoretically promote uptake by dendritic cells, and cause high immunogenicity. To test for this, mice were immunised with 50 nm (i.e. 0.05 µm) particles having different charges on the surface. OVA-VSSP has an overall negative charge due to use of carboxylate modified nanoparticles and quenching the activated carboxylic acid groups after conjugation of OVA with glycine (Glycine FIG. 19). By quenching the reaction with ethanolamine charges can be neutralised except for the net charge of OVA after conjugation (Alcohol, FIG. 19). By quenching with ethylenediamine a positive charge is introduced (Amine, FIG. 19). By quenching with aminoacetaldehyde dimethyl acetal (Aldehyde, FIG. 19) potentially useful aldehyde groups can be introduced. All three modifications of the conjugation protocol resulted in highly immunogenic particles, with amine and alcohol modifications being comparable to glycine, and aldehyde slightly less immunogenic. Therefore it is highly unlikely immunogenicity results from non-specific adsorption of serum proteins as the introduction of opposite charges to the particle results in similar immunogenicity. Moreover, some alternative modifications to the conjugation procedure, and changes in charges can be introduced with no decrease in immunogenicity.

Discussion

In view of the results above, the composition of the invention provides a way to further improve or optimise vaccines or vaccination strategy that could apply to a variety of infections, cancer or other diseases.

The optimal size of the VSSP coincides with that of most known viruses (30-150 nm). Hence, it is tempting to speculate that use of the VSSPs is biologically significant. From the above observations, the inventor believes that the immune system may be geared to react fully to particles of the size range of the VSSPs. Before the present invention, it was not known or understood that the stimulation of an immune response could depend to a great extent on the size of an immune stimulant that falls within the size range of viruses, especially when epitopes from other pathogens eg bacteria, fungi are considerably large. Indeed, antigens targeted through this pathway elicited surprisingly broad (comprising both humoral and cellular arms of the immune response) and strong responses (inducing rapidly long lasting high effector T cell precursor frequencies) suggesting the immune system may be geared to react fully to particles of viral size. Previous studies utilising VLPs (i.e. pure antigen not linked to a particle) comprised of HepB surface proteins, or the yeast retrotransposon protein (Ty) have also shown broad and long lasting immunity induced by a single immunizing dose, although responses were still 10-100 fold lower than with VSSPs [1, 2, 3, 19, 20]. However it has been assumed that characteristics other than size alone, such as their lipid or mannan content, or membrane biding proteins are responsible for the ability of VLPs to induce class I restricted T cell responses [1]. Not wishing to be bound by theory, the inventor considers that the combination of efficient targeting to antigen presenting cells such as dendritic cells in vivo by VSSPs, followed by potential slow antigen release by proteolysis from VSSPs, may have generated particularly powerful immunogens.

Use of VSSP as novel vaccines was demonstrated by the ability of a single immunising dose to protect against subsequent challenge with tumor cells in the OVA model. The inventor has also observed broad and strong immunogenicity and protection to an antigen expressed in breast cancer, mucin-1 (MUC-1). The intradermal route of administration utilised in their animal studies may be easily implemented in humans. VSSPs may thus offer a particularly attractive and simple strategy for human vaccine development, in particular to diseases where both humoral and cellular immunity participate in generating protection, such as malaria, cancer and viral diseases, notably, AIDS and hepatitis [10, 12, 21, 25-28]. The targeting of recombinant antigen to class I presentation pathway also offers the possibility of inducing T cell responses to multiple epitopes, and thus would extend the use of such vaccines in a MHC diverse target human population.

At present, priming of DCs for effective stimulation of CTLs is by ex vivo pulsing of DCs but this is expensive and logistically difficult. The present invention provides an alternative to efficiently deliver antigens to DCs in vivo, leading to the subsequent induction of high numbers of antigen specific CD8 T-cells and immune protection. The ability of the VSSPs within the narrow size range of 0.04-0.05 µm to induce singularly high CD8 T-cell levels could be the consequence of efficient uptake by APCs or by a potent subset, targeting to the MHC 1 processing pathway and/or direct stimulation of APC function. Uptake of the VSSPs was found to be enhanced in the lymph node, compared to other sizes, and this enhancement was attributed to increased frequencies of particle positive DEC205+ cells, a marker of DCs. DCs are powerful APC and expression of CD40 and CD86 further characterises a subset capable of efficient CD8 T-cell priming. These markers were found in a high proportion of VSSP+ cells. Thus, uptake and selective localisation of VSSP in this potent DC subset in vivo could explain the immunogenicity of the microparticles according to the invention.

Other advantages of the VSSP of the invention include the ability to induce immune responses including IgA production following administration via a number of routes, and their suitability for prime-boost vaccination strategy.

Further studies will involve the use of the VSSPs to determine the physiological mechanisms that make them elicit the unique immune response obtained.

It is to be understood that various other embodiments of the invention that is described herein may be made by those skilled in the art without departing from the central concept underlying the invention.

REFERENCES

1. Reimann J, Shirmbeck R. Alternative pathways for processing exogenous and endogenous antigens that can generate peptides for MHC class I-restricted presentation. Immunol. Rev. 1999; 172:131-152.
2. Schirmbeck R, Melber K, Reimann J. Hepatitis B virus small surface antigen particles are processed in a novel endosomal pathway for major histocompatibility complex class I-restricted epitope presentation. Eur. J. Immunol. 1995; 25:1063-1070.
3. Plebanski M, Gilbert S C, Schneider J, Hannan C M, Layton G, Blanchard T, Becker M, Smith G, Butcher G, Sinden R E, Hill A V. Protection from *Plasmodium berghei* infection by priming and boosting T cells to a single class I-restricted epitope with recombinant carriers suitable for human use. Eur J Immunol 1998; 28:4345-55.
4. (P. Johansen, B. Gander, H P Merkle and D Sesardic, Ambiguities in the Preclinical Quality Assessment of Microparticulate Vaccines, TIBTECH 2000, 18:203).
5. Lu L, McCaslin D, Starzl T E, Thomson A W. Bone marrow-derived dendritic cell progenitors (NLDC 145+, MHC class II+, B7-1dim, B7-2-) induce alloantigen-specific hyporesponsiveness in murine T lymphocytes. Transplantation 1995; 60:1539-45.
6. Plebanski. Preparation of lymphocytes and identification of lymphocyte subpopulations in Lymphocytes: a practical approach 1999; Edited by Rowland-Jones, S L and McMichael, A J: 1-26.
7. Pietersz G A, Li W, Popovski V, Caruana J-A, Apostolopoulos V, McKenzie IFC. Parameters for using mannan-MUC1fusion protein to induce cellular immunity. Cancer Immunol Immunother 1998; 45:321-326.
8. Fazekas de St. Groth S. The evaluation of limiting dilution assays. J Immunol Methods 1982; 49:R11.
9. Lefkovits I, Waldmann H. Limiting dilution analysis of the cells of the immune system. I. The clonal basis of the immune response. Immunol Today 1984; 5:265.
10. York I A, Rock K L. Antigen processing and presentation by the class I major histocompatibility complex. Annu Rev Immunol 1996; 14:369-96.
11. Falo L D, Jr., Kovacsovics-Bankowski M, Thompson K, Rock K L. Targeting antigen into the phagocytic pathway in vivo induces protective tumour immunity. Nat Med 1995; 1:649-53.
12. Robinson S P, Saraya K, Reid C D. Developmental aspects of dendritic cells in vitro and in vivo. Leuk Lymphoma 1998; 29:477-90.
13. Mosleh I M, Hubers L A, Steinlein P, Pasquali C, Gunther D, Meyer T F. *Neisseria gonorrhoeae* porin modulates phagosome maturation. J. Biol. Chem. 1998; 273:35332-35338.
14. Lamaze, Ch. & Schmid, S. L. The emergence of clathrin-independent pinocytic pathways Curr. Opin. Cell Biol. 7, 573-80 (1995).
15. Werling, D. et al. Involvement of caveolae in the uptake of respiratory syncytial virus antigen by dendritic cell. J. Leukoc Biol 66, 50-8 (1999).
16. Schnitzer, J. E., Oh, P., Pinney, E. & Allard, J. Filipin-sensitive caveolae-mediated transport in endothelium: reduced transcytosis, scavenger endocytosis, and capillary permeability of select macromolecules. J Cell Biol 127, 1217-32 (1994).
17. Anderson, R. G. Caveolae: where incoming and outgoing messengers meet. Proc Natl Acad Sci USA 90, 10909-13 (1993).
18. Reimann, J. & Kaufmann, S. H. Alternative antigen processing pathways in anti-infective immunity [see comments]. Curr Opin Immunol 9, 462-9 (1997).
19. Gilbert S C, Plebanski M, Harris S J, Allsopp C E, Thomas R, Layton G T, Hill A V. A protein particle vaccine containing multiple malaria epitopes. Nat Biotechnol 1997; 15:1280-4.
20. Gilbert S C, Schneider J, Plebanski M, Hannan C M, Blanchard T J, Smith G L, Hill A V. Ty virus-like particles, DNA vaccines and Modified Vaccinia Virus Ankara; comparisons and combinations. Biol Chem 1999; 380:299-303.
21. Plebanski M, Hill A V S. The immunology of malaria infection. Curr. Opin. Immunol. 2000; 12:437-441.
22. Apostolopoulos V, McKenzie I F, Pietersz G A. Breast cancer immunotherapy: current status and future prospects. Immunol Cell Biol 1996; 74:457-64.
23. Cook G, Campbell J D. Immune regulation in multiple myeloma: the host-tumour conflict. Blood Rev 1999; 13:151-62.
24. Gupta R K, Singh M, OHagan D T. Poly (lactide-co-glycolide) microparticles for the development of single-dose controlled-release vaccines. Adv. Drug Deliv. Rev. 1998; 32:225-246.
25. Chisari F V, Ferrari C. Hepatitis B virus immunopathogenesis. Annu Rev. Immunol. 1995; 13:29-60.
26. Pierson T, McArthur J, Siciliano R F. Reservoirs for HIV: mechanisms for viral persistence in the presence of antiviral immune responses and anti-retroviral therapy. Annu. Rev. Immunol. 2000; 18:665-708.
27. Harty J T, Tvinnereim A R, White D W. CD8+ T cell effector mechanisms in resistance to infection. Annu Rev. Immunol. 2000; 18.
28. Boehm U., Klamp T., Groot M., Howard J. C. Cellular responses to interferongamma. Annu Rev Immunol 1997; 15:749-95.
29. Arnold-Schild, D. et al. Cutting edge: receptor-mediated endocytosis of heat shock proteins by professional antigen-presenting cells. J. Immunol. 162, 3757-60 (1999).

What is claimed is:

1. A method of stimulating uptake of an antigen by dendritic cells in vivo in a mammalian subject, comprising administering to the subject a composition comprising synthetic viral-sized particles having solid cores and having the antigen covalently bound to their outer surface, wherein the viral-sized particles have an average diameter of from 0.030 µm to 0.100 µm, wherein the composition is administered to the mammalian subject so as to facilitate contact of the viral-sized particles with the dendritic cells, thereby stimulating uptake of the antigen by the dendritic cells, wherein the antigen is selected from the group consisting of peptide, protein, lipid, carbohydrate, and combinations thereof.

2. The method of claim 1, wherein the viral-sized particles have an average diameter of from about 0.030 µm to about 0.050 µm.

3. The method of claim 1, wherein the viral-sized particles have an average diameter of from about 0.040 µm to about 0.050 µm.

4. The method of claim 1, wherein the viral-sized particles are of substantially uniform size.

5. The method of claim 1, wherein the viral-sized particles comprise a solid core.

6. The method of claim 1, wherein the dendritic cells are DEC205+, CD40+ and CD86+.

7. The method of claim 1, wherein the viral-sized particles are selected from the group consisting of latex, ferrous molecules, gold, glass, calcium phosphate, polystyrene, polylysine G, biodegradable polymers, biocompatible polymers, and combinations thereof.

8. The method of claim 1, wherein the antigen is from a pathogen, tissue, cell organ or molecule and is selected from the group consisting of: pollen, hepatitis C virus (HIV) core, E1, E2 and NS2 proteins, antigens from *Plasmodium* species selected from the group consisting of *P. vivax, P. falciparum* circumsporozoite protein (CS), human *P. falciparum, P. vivax, P. ovalae,* and *P. malariae,* TRAP, MSP-1, MSP-2, MSP-3, MSP-4, MSP-5, AMA-1 RESA, SALSA, STARP, LSA1 and LSA3, HIV-gp120/160 envelope glycoprotein, *streptococcus* surface protein antigen, influenza nucleoprotein, hemagglutinin-neuraminidase surface infection, TcpA pilin subunit, VP1 protein, LMCV nucleoprotein, *Leishmania major* surface glycoprotein (gp63), *Bordetella pertussis* surface protein, rabies virus G protein, *Streptococcus* M protein, Staphylococcal proteins, *Helicobacter pylori* proteins, Syncytial virus (RSV) F or G proteins, Epstein Ban virus (EBV) gp340 or nucleoantigen 3A, hemagglutinin, *Borrelia burgdoferi* outer surface protein (Osp) A, *Mycobacterium tuberculosis* 38 kD lipoprotein or 30 kD protein (Ag85), 10 kD or 65 kD proteins, *Neisseria meningitidis* class 1 outer protein, Varicella zoster virus IE62 and gpl, Rubella virus capsid protein, Hepatitis B virus pre S1 ag, Herpes simplex virus type 1 glycoprotein G or gp D or CP27, Murray valley encephalitis virus E glycoprotein, Hepatitis A virus VP1, polio virus capsid protein VP1, VP2 and VP3, *Chlamydia trachomatis* surface protein, Hepatitis B virus envelope Ag pre S2, Human rhinovirus (HIV) capsid, papillomavirus peptides from oncogene E6 and E7, *Listeria* surface protein, Varicella virus envelope protein, Vaccinia virus envelope protein, *Brucella* surface protein, Rotavirus, VP-3, VP-4, VP-5, VP-7 and VP-8, a combination of one or more of the antigens, an amino acid subunit of the antigen comprising five or more amino acids in length, and combinations of one or more of the subunits.

9. The method of claim 1, wherein the antigen is a cancer antigen.

10. The method of claim 9, wherein the cancer antigen is selected from the group consisting of a breast cancer antigen, a lung cancer antigen, a pancreatic cancer antigen, a colon cancer antigen, and a melanoma cancer antigen.

11. The method of claim 1, wherein the composition is administered to the subject orally, by inhalation, by administration through a mucosal surface or site or by injection subcutaneously, intra-dermally, intra-muscularly, intra-peritoneally, or intra-venously.

12. The method of claim 11, wherein the composition is administered to the subject by injection subcutaneously, intra-dermally, intra-muscularly, or intra-peritoneally, and wherein the composition is capable of promoting a cellular immune response to the antigen in the absence of added adjuvant.

13. The method of claim 1, wherein the uptake of the antigen by the dendritic cells promotes proliferation and/or expansion and/or maturation of the dendritic cells.

14. The method of claim 1, wherein the uptake of the antigen by the dendritic cells promotes a cellular immune response to the antigen in the subject, and wherein the composition is capable of promoting a cellular immune response to the antigen in the absence of added adjuvant.

15. The method of claim 14, wherein the cellular immune response to the antigen is elicited following a single administration of the composition.

16. The method of claim 14, wherein the cellular immune response to the antigen includes a CD8 T cell immune response to the antigen.

17. The method of claim 14, wherein the uptake of the antigen by the dendritic cells further promotes a humoral response to the antigen, wherein the humoral response is selected from immunoglobulin G, immunoglobulin M or immunoglobulin A to the antigen.

18. The method of claim 1, wherein the viral-sized particles are polystyrene.

19. The method of claim 1, wherein, following covalent attachment of the antigen, the viral-sized particles were quenched with a quenching agent selected from glycine, an alcohol, an amine, or an aldehyde.

20. The method of claim 19, wherein the quenching agent was glycine.

21. A method of stimulating uptake of an antigen by dendritic cells in vivo in a mammalian subject, comprising administering to the subject a composition comprising an effective amount of viral-sized particles of polystyrene or glass having an average diameter of from 0.030 µm to 0.100 µm and the antigen covalently bound to their outer surface, wherein the composition is administered to the subject so as to facilitate contact of the viral-sized particles with the dendritic cells, thereby stimulating uptake of the antigen by the dendritic cells, wherein the antigen is selected from the group consisting of peptide, protein, lipid, carbohydrate, and combinations thereof.

22. The method of claim 21, wherein the viral-sized particles have an average diameter of from about 0.030 µm to about 0.050 µm.

23. The method of claim 21, wherein, following covalent attachment of the antigen, the viral-sized particles were quenched with a quenching agent selected from glycine, an alcohol, an amine, or an aldehyde.

24. A method of stimulating a CD8 T cell immune response to an antigen in a mammalian subject, comprising administering to the subject a composition comprising an effective amount of synthetic viral-sized particles having the antigen covalently bound to their outer surface, wherein the viral-sized particles have an average diameter of from 0.030 μm to 0.100 μm, wherein the antigen is selected from the group consisting of peptide, protein, lipid, carbohydrate, and combinations thereof, and wherein the composition is capable of promoting the cellular immune response in the absence of added adjuvant.

* * * * *

```
SEQUENCE LISTING

<160> NUMBER OF SEQ ID NOS: 1

<210> SEQ ID NO 1
<211> LENGTH: 8
<212> TYPE: PRT
<213> ORGANISM: Artificial
<220> FEATURE:
<223> OTHER INFORMATION: Synthetic

<400> SEQUENCE: 1

Ser Ile Ile Asn Phe Glu Lys Leu
 1               5
```